(12) United States Patent
Kew et al.

(10) Patent No.: US 7,547,676 B2
(45) Date of Patent: Jun. 16, 2009

(54) ANTAGONIST PEPTIDES TO THE C5A CHEMOTACTIC FUNCTION OF VITAMIN D BINDING PROTEIN

(75) Inventors: Richard R. Kew, Miller Place, NY (US); Jianhua Zhang, Stony Brook, NY (US)

(73) Assignee: The Research Foundation of State University of New York, Albany, NY (US)

( * ) Notice: Subject to any disclaimer, the term of this patent is extended or adjusted under 35 U.S.C. 154(b) by 270 days.

(21) Appl. No.: 11/243,960

(22) Filed: Oct. 5, 2005

(65) Prior Publication Data

US 2006/0094659 A1 May 4, 2006

Related U.S. Application Data

(60) Provisional application No. 60/616,105, filed on Oct. 5, 2004.

(51) Int. Cl.
*A61K 38/10* (2006.01)
*A61K 38/07* (2006.01)
(52) U.S. Cl. ............... 514/13; 514/14; 514/15; 514/16; 514/17; 514/18; 530/326; 530/327; 530/328; 530/329; 530/330
(58) Field of Classification Search ............... None
See application file for complete search history.

(56) References Cited

U.S. PATENT DOCUMENTS 5,326,749 A * 7/1994 Yamamoto ............... 514/8
5,808,109 A * 9/1998 Sindelar et al. ............ 549/345

OTHER PUBLICATIONS

Kurata et al. 'Analysis of Peptide Residues Interacting With MHC Molecule or T Cell Receptor.' J. of Immun. vol. 144, No. 12, pp. 4526-4535. Jun. 1990.*
White, P. et al., "The Multifunctional Properties and Characteristics of Vitamin D-binding Protein", *TEM 11*(8): 320-327 (2000).
Gomme, P. T. et al., "Therapeutic potential of vitamin D-binding protein", *Trends in Biotechnology 22*(7): 340-345 (2004).
Hirschfeld, J., "Immune-Electrophoretic Demonstration Of Qualitative Differences In Human Sera And Their Relation To The Haptoglobins", *Acta Path. 47*(2): 160-168 (1959).
Haddad, J. G. et al., "Identification of the Sterol- and Actin-Binding Domains of Plasma Vitamin D Binding Protein (Gc-Globulin)", *Biochemistry 31*: 7174-7181 (1992).
Swamy, N. et al., "Roles of the Structure and Orientation of Ligands and Ligand Mimics inside the Ligand-Binding Pocket of the Vitamin D-Binding Protein", *Biochemistry 36*: 7432-7436 (1997).
Verboven, C. et al., "A structural basis for the unique binding features of the human vitamin D-binding protein", *Nature Structural Biology 9*(2): 131-136 (2002).

Swamy, N. et al., "Biochemical and preliminary crystallographic characterization of the vitamin D sterol- and actin-binding by human vitamin D-binding protein", *Archives of Biochemistry and Biophysics 402*: 14-23 (2002).
Head, J. F. et al., "Crystal Structure of the Complex between Actin and Human Vitamin D-Binding Protein at 2.5 Å Resolution", *Biochemistry 41*: 9015-9020 (2002).
Otterbein, L. R. et al., "Crystal structures of the vitamin D-binding protein and its complex with actin: Structural basis of the actin-scavenger system", *PNAS 99*(12): 8003-8008 (2002).
Köhl, Jög, "Anaphylatoxins and infectious and non-infectious inflammatory dieases", *Molecular Immunology 38*: 175-187 (2001).
Gerard, N. P. et al., "The chemotactic receptor for human C5a anaphylatoxin", *Nature 349*: 614-617 (1991).
Kew, R. R. et al., "Gc-Globulin (Vitamin D-binding Protein) Enhances the Neutrophil Chemotactic Activity of C5a and C5a des Arg", *J. Clin. Invest. 82*: 364-369 (1988).
Perez, H. D. et al., "Identification of the C5a des Arg Cochemotaxin", *J. Clin. Invest. 82*: 360-363 (1988).
Petrini, M. et al., "1,25-dihydroxycholecalciferol inhibits the cochemotactic activity of Gc (vitamin D binding protein)", *J. Endocrinol. Invest. 14*: 405-408 (1991).
Metcalf, J. P. et al., "GcGlobulin Functions as a Cochemotaxin in the Lower Respiratory Tract", *Am. Rev. Respir. Dis. 143*: 844-849 (1991).
Binder, R. et al., "Neutrophil priming by cytokines and vitamin D binding protein (Gc-globulin): impact on C5a-mediated chemotaxis, degranulaton and respiratory burst", *Molecular Immunology 36*: 885-892 (1999).
Zwahlen, R. D. et al., "Chemotactic Competence Of Neutrophils From Neonatal Calves", *Inflammation 14*(1): 109-123 (1990).
Piquette, C. A. et al., "Human monocyte chemotaxis to complement-derived chemotaxins is enhanced by Gc-globulin", *J. Leukoc. Biol. 55*: 349-354 (1994).
Senior, R. M. et al., "Human C5a And C5a Des Arg Exhibit Chemotactic Activity For Fibroblasts", *J. Immunol. 141*: 3570-3574 (1988).
Trujillo, G. et al., "Platelet-Derived Thrombospondin-1 Is Necessary for the Vitamin D-Binding Protein (Gc-Globulin) to Function as a Chemotactic Cofactor for C5a[1]", *J. Immunol. 173*: 4130-4136 (2004).

(Continued)

*Primary Examiner*—Anish Gupta
(74) *Attorney, Agent, or Firm*—Scully, Scott, Murphy & Presser, P.C.

(57) ABSTRACT

It has been demonstrated that one of Vitamin D Binding Protein (DBP) biological functions is to enhance the chemotactic activity of C5*a* and C5*a* des Arg. The present invention has found that peptides having sequences that substantially correspond to a specific region in the N-terminal domain I of DBP can block the DBP enhancement of C5*a* or C5*a* des Arg chemotactic activity. Based in this discovery the present invention provides DBP antagonist peptides and the use thereof for the treatment C5*a* or C5*a* des Arg-mediated disorders.

4 Claims, 15 Drawing Sheets

OTHER PUBLICATIONS

Figure 1:
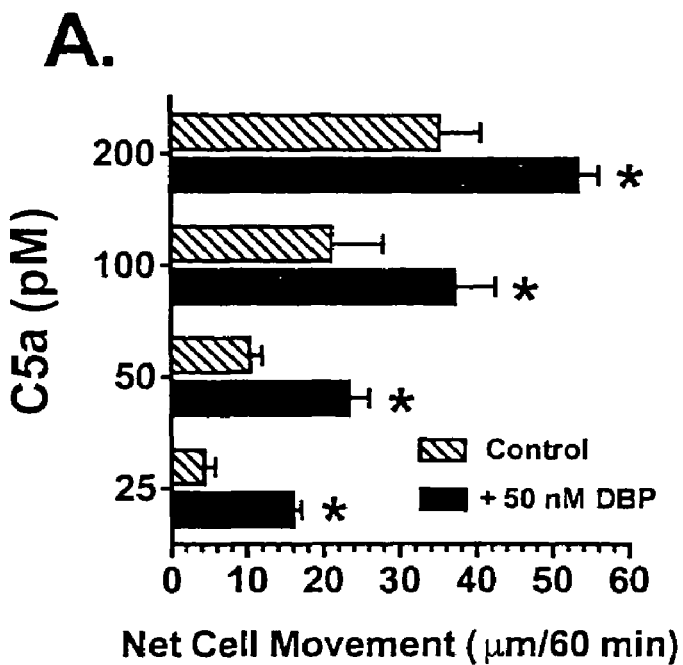
Figure 1:
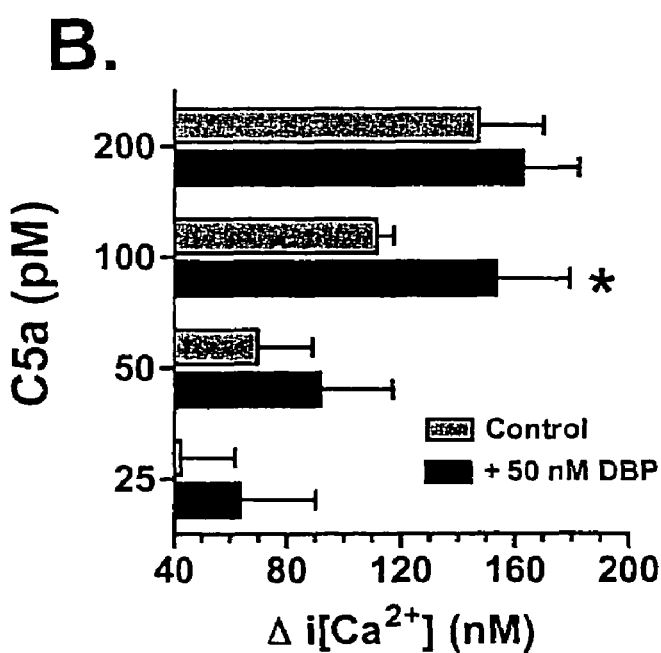

Swamy N. et al., "Bacterial Expression of Human Vitamin D-Binding Protein (Gc2) in Functional Form[1,2]", *Protein Expression and Purification 10*: 115-122 (1997).

Merritt, J. E. et al., "Use of fluo-3 to measure cytosolic $CA^{2+}$ in platelets and neutrophils", *Biochem. J. 269*: 513-519 (1990).

Kew, R. R. et al., "Binding of Gc globulin (vitamin D binding protein to C5a or C5a des Arg is not necessary for co-chemotactic activity", *Journal of Leukocyte Biology 58*: 55-58 (1995).

Zigmond, S. H. et al., "Leukocyte Locomotion And Chemotaxis", *The Journal of Experimental Medicine 137*: 387-410 (1973).

Kew, R. R. et al., "Co-Chemotactic Effect of Gc-Globulin (Vitamin D Binding Protein) for C5a", *The Journal of Immunology 155*: 5369-5374 (1995).

Cooke, N. E., "Rat Vitamin D Binding Protein", *The Journal of Biological Chemistry*, 261 (7): 3441-3450 (1986).

Yang, F. et al., "Mapping and Conservation of the Group-Specific Component Gene in Mouse", *Genomics 7*: 509-516 (1990).

Osawa, M. et al., "Cloning And Sequence Analysis Of cDNA Encodign Rabbit Vitamin D-Binding Protein (GC Globulin)", *Biochemistry and Molecular Biology International 34*(5): 1003-1009 (1994).

He, X. M. et al., "Atomic structure and chemistry of human serum albumin", *Nature 358*: 209-215 (1992).

Mizwicki, M. et al., "Two Key Proteins of the Vitamin D Endocrine System Come Into Crystal Clear Focus: Comparison of the X-ray Structures of the Nuclear Receptor for 1 $\alpha$,25 $(OH)_2$ Vitamin $D_3$, the Plasma Vitamin D Binding Protein, and Their Ligands", *Journal of Bone and Mineral Research 18*(5): 795-806 (2003).

Di Martino, S. J. et al., "Initial Characterization of the Vitamin D Binding Protein (Gc-Globulin) Binding Site on the Neutrophil Plasma Membrane: Evidence for a Chondroitin Sulfate Proteoglycan[1]", *The Journal of Immunology 163*: 2135-2142 (1999).

Nykjaer, A. et al., "An Endocytic Pathway Essential for Renal Uptake and Activation of the Steroid 25-(OH) Vitamin $D_3$", *Cell 96*: 507-515 (1999).

Nykjaer, A. et al., "Cubilin dysfunction causes abnormal metabolism of the steroid hormone 25(OH) vitamin $D_3$", *PNAS 98*(24): 13895-13900 (2001).

Kanda, S. et al., "Effects of Vitamin $D_3$-Binding Protein-Derived Macrophage Activating Factor (GcMAF) on Angiogenesis", *Journal of the National Cancer Institute 94*(17): 1311-1319 (2002).

Licht, P. et al., "Identification and Structural characterization of a novel member of the virtamin D binding protein family", *Comp. Biochem. Physiol.* (2001), Abstract.

McVoy, L. A. et al., "CD44 and Annexin A2 Mediate the C5a Chemotactic Cofactor Function of the Vitamin D Binding Protein[1]", *The Journal of Immunology 175*: 4754-4760 (2005).

* cited by examiner

SEQUENCE LISTING

<160> NUMBER OF SEQ ID NOS: 38

<210> SEQ ID NO 1
<211> LENGTH: 20
<212> TYPE: PRT
<213> ORGANISM: Artificial Sequence
<220> FEATURE:
<223> OTHER INFORMATION: synthetic peptide

<400> SEQUENCE: 1

Glu Ala Phe Arg Lys Asp Pro Lys Glu Tyr Ala Asn Gln Phe Met Trp
1               5                   10                  15

Glu Tyr Ser Thr
            20

<210> SEQ ID NO 2
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid

```
<220> FEATURE:
<221> NAME/KEY: misc_feature
<222> LOCATION: (20)..(20)
<223> OTHER INFORMATION: Xaa can be any naturally occurring amino acid

<400> SEQUENCE: 2

Glu Ala Phe Xaa Xaa Asp Pro Xaa Xaa Xaa Ala Xaa Xaa Phe Xaa Xaa
1               5                   10                  15

Glu Tyr Ser Xaa
            20

<210> SEQ ID NO 3
<211> LENGTH: 23
<212> TYPE: PRT
<213> ORGANISM: Artificial Sequence
<220> FEATURE:
<223> OTHER INFORMATION: synthetic peptide

<400> SEQUENCE: 3

Glu Ala Phe Arg Lys Asp Pro Lys Glu Tyr Ala Asn Gln Phe Met Trp
1               5                   10                  15

Glu Tyr Ser Thr Asn Tyr Gly
            20

<210> SEQ ID NO 4
<211> LENGTH: 23
<212> TYPE: PRT
<213> ORGANISM: Artificial Sequence
<220> FEATURE:
<223> OTHER INFORMATION: synthetic peptide

<400> SEQUENCE: 4

Asn Tyr Gly Gln Ala Pro Leu Ser Leu Leu Val Ser Tyr Thr Lys Ser
1               5                   10                  15

Tyr Leu Ser Met Val Gly Ser
            20

<210> SEQ ID NO 5
<211> LENGTH: 19
<212> TYPE: PRT
<213> ORGANISM: Artificial Sequence
<220> FEATURE:
<223> OTHER INFORMATION: synthetic peptide

<400> SEQUENCE: 5

Glu Ala Phe Arg Lys Asp Pro Lys Glu Tyr Ala Asn Gln Phe Met Trp
1               5                   10                  15

Glu Tyr Ser

<210> SEQ ID NO 6
<211> LENGTH: 15
<212> TYPE: PRT
<213> ORGANISM: Artificial Sequence
<220> FEATURE:
<223> OTHER INFORMATION: synthetic peptide

<400> SEQUENCE: 6

Glu Ala Phe Arg Lys Asp Pro Lys Glu Tyr Ala Asn Gln Phe Met
1               5                   10                  15

<210> SEQ ID NO 7
<211> LENGTH: 15
<212> TYPE: PRT
<213> ORGANISM: Artificial Sequence
<220> FEATURE:
```

```
<223> OTHER INFORMATION: synthetic peptide

<400> SEQUENCE: 7

Asp Pro Lys Glu Tyr Ala Asn Gln Phe Met Trp Glu Tyr Ser Thr
1               5                   10                  15

<210> SEQ ID NO 8
<211> LENGTH: 12
<212> TYPE: PRT
<213> ORGANISM: Artificial Sequence
<220> FEATURE:
<223> OTHER INFORMATION: synthetic peptide

<400> SEQUENCE: 8

Glu Ala Phe Arg Lys Asp Pro Lys Glu Tyr Ala Asn
1               5                   10

<210> SEQ ID NO 9
<211> LENGTH: 12
<212> TYPE: PRT
<213> ORGANISM: Artificial Sequence
<220> FEATURE:
<223> OTHER INFORMATION: synthetic peptide

<400> SEQUENCE: 9

Asp Pro Lys Glu Tyr Ala Asn Gln Phe Met Trp Glu
1               5                   10

<210> SEQ ID NO 10
<211> LENGTH: 12
<212> TYPE: PRT
<213> ORGANISM: Artificial Sequence
<220> FEATURE:
<223> OTHER INFORMATION: synthetic peptide

<400> SEQUENCE: 10

Asn Gln Phe Met Trp Glu Tyr Ser Thr Asn Tyr Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: synthetic peptide

<400> SEQUENCE: 11

Tyr Ala Asn Gln Phe Met Trp Glu Tyr Ser Thr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: synthetic peptide

<400> SEQUENCE: 12

Glu Ala Phe Arg Lys Asp Pro Lys Glu Tyr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: synthetic peptide
```

-continued

<400> SEQUENCE: 13

Ala Asn Gln Phe Met Trp Glu Tyr Ser Thr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: synthetic peptide

<400> SEQUENCE: 14

Asp Pro Lys Glu Tyr Ala Asn Gln Phe Met
1               5                   10

<210> SEQ ID NO 15
<211> LENGTH: 9
<212> TYPE: PRT
<213> ORGANISM: Artificial Sequence
<220> FEATURE:
<223> OTHER INFORMATION: synthetic peptide

<400> SEQUENCE: 15

Asn Gln Phe Met Trp Glu Tyr Ser Thr
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic peptide

<400> SEQUENCE: 16

Asn Gln Phe Met Trp Glu Tyr Ser
1               5

<210> SEQ ID NO 17
<211> LENGTH: 8
<212> TYPE: PRT
<213> ORGANISM: Artificial Sequence
<220> FEATURE:
<223> OTHER INFORMATION: synthetic peptide

<400> SEQUENCE: 17

Gln Phe Met Trp Glu Tyr Ser Thr
1               5

<210> SEQ ID NO 18
<211> LENGTH: 7
<212> TYPE: PRT
<213> ORGANISM: Artificial Sequence
<220> FEATURE:
<223> OTHER INFORMATION: synthetic peptide

<400> SEQUENCE: 18

Asn Gln Phe Met Trp Glu Tyr
1               5

<210> SEQ ID NO 19
<211> LENGTH: 7
<212> TYPE: PRT
<213> ORGANISM: Artificial Sequence
<220> FEATURE:
<223> OTHER INFORMATION: synthetic peptide

```
<400> SEQUENCE: 19

Gln Phe Met Trp Glu Tyr Ser
1               5

<210> SEQ ID NO 20
<211> LENGTH: 7
<212> TYPE: PRT
<213> ORGANISM: Artificial Sequence
<220> FEATURE:
<223> OTHER INFORMATION: synthetic peptide

<400> SEQUENCE: 20

Phe Met Trp Glu Tyr Ser Thr
1               5

<210> SEQ ID NO 21
<211> LENGTH: 6
<212> TYPE: PRT
<213> ORGANISM: Artificial Sequence
<220> FEATURE:
<223> OTHER INFORMATION: synthetic peptide

<400> SEQUENCE: 21

Glu Ala Phe Arg Lys Asp
1               5

<210> SEQ ID NO 22
<211> LENGTH: 6
<212> TYPE: PRT
<213> ORGANISM: Artificial Sequence
<220> FEATURE:
<223> OTHER INFORMATION: synthetic peptide

<400> SEQUENCE: 22

Lys Glu Tyr Ala Asn Gln
1               5

<210> SEQ ID NO 23
<211> LENGTH: 6
<212> TYPE: PRT
<213> ORGANISM: Artificial Sequence
<220> FEATURE:
<223> OTHER INFORMATION: synthetic peptide

<400> SEQUENCE: 23

Tyr Ala Asn Gln Phe Met
1               5

<210> SEQ ID NO 24
<211> LENGTH: 6
<212> TYPE: PRT
<213> ORGANISM: Artificial Sequence
<220> FEATURE:
<223> OTHER INFORMATION: synthetic peptide

<400> SEQUENCE: 24

Ala Asn Gln Phe Met Trp
1               5

<210> SEQ ID NO 25
<211> LENGTH: 6
<212> TYPE: PRT
<213> ORGANISM: Artificial Sequence
<220> FEATURE:
<223> OTHER INFORMATION: synthetic peptide

<400> SEQUENCE: 25
```

```
Asn Gln Phe Met Trp Glu
1               5
```

<210> SEQ ID NO 26
<211> LENGTH: 6
<212> TYPE: PRT
<213> ORGANISM: Artificial Sequence
<220> FEATURE:
<223> OTHER INFORMATION: synthetic peptide

<400> SEQUENCE: 26

```
Gln Phe Met Trp Glu Tyr
1               5
```

<210> SEQ ID NO 27
<211> LENGTH: 6
<212> TYPE: PRT
<213> ORGANISM: Artificial Sequence
<220> FEATURE:
<223> OTHER INFORMATION: synthetic peptide

<400> SEQUENCE: 27

```
Phe Met Trp Glu Tyr Ser
1               5
```

<210> SEQ ID NO 28
<211> LENGTH: 5
<212> TYPE: PRT
<213> ORGANISM: Artificial Sequence
<220> FEATURE:
<223> OTHER INFORMATION: synthetic peptide

<400> SEQUENCE: 28

```
Glu Ala Phe Arg Lys
1               5
```

<210> SEQ ID NO 29
<211> LENGTH: 5
<212> TYPE: PRT
<213> ORGANISM: Artificial Sequence
<220> FEATURE:
<223> OTHER INFORMATION: synthetic peptide

<400> SEQUENCE: 29

```
Ala Phe Arg Lys Asp
1               5
```

<210> SEQ ID NO 30
<211> LENGTH: 5
<212> TYPE: PRT
<213> ORGANISM: Artificial Sequence
<220> FEATURE:
<223> OTHER INFORMATION: synthetic peptide

<400> SEQUENCE: 30

```
Asp Pro Lys Glu Tyr
1               5
```

<210> SEQ ID NO 31
<211> LENGTH: 5
<212> TYPE: PRT
<213> ORGANISM: Artificial Sequence
<220> FEATURE:
<223> OTHER INFORMATION: synthetic peptide

<400> SEQUENCE: 31

```
Ala Asn Gln Phe Met
1               5

<210> SEQ ID NO 32
<211> LENGTH: 5
<212> TYPE: PRT
<213> ORGANISM: Artificial Sequence
<220> FEATURE:
<223> OTHER INFORMATION: synthetic peptide

<400> SEQUENCE: 32

Trp Glu Tyr Ser Thr
1               5

<210> SEQ ID NO 33
<211> LENGTH: 5
<212> TYPE: PRT
<213> ORGANISM: Artificial Sequence
<220> FEATURE:
<223> OTHER INFORMATION: synthetic peptide

<400> SEQUENCE: 33

Tyr Ala Asn Gln Phe
1               5

<210> SEQ ID NO 34
<211> LENGTH: 5
<212> TYPE: PRT
<213> ORGANISM: Artificial Sequence
<220> FEATURE:
<223> OTHER INFORMATION: synthetic peptide

<400> SEQUENCE: 34

Ala Asn Gln Phe Met
1               5

<210> SEQ ID NO 35
<211> LENGTH: 5
<212> TYPE: PRT
<213> ORGANISM: Artificial Sequence
<220> FEATURE:
<223> OTHER INFORMATION: synthetic peptide

<400> SEQUENCE: 35

Asn Gln Phe Met Trp
1               5

<210> SEQ ID NO 36
<211> LENGTH: 5
<212> TYPE: PRT
<213> ORGANISM: Artificial Sequence
<220> FEATURE:
<223> OTHER INFORMATION: synthetic peptide

<400> SEQUENCE: 36

Gln Phe Met Trp Glu
1               5

<210> SEQ ID NO 37
<211> LENGTH: 5
<212> TYPE: PRT
<213> ORGANISM: Artificial Sequence
<220> FEATURE:
<223> OTHER INFORMATION: synthetic peptide

<400> SEQUENCE: 37

Phe Met Trp Glu Tyr
```

```
1               5
```

```
<210> SEQ ID NO 38
<211> LENGTH: 5
<212> TYPE: PRT
<213> ORGANISM: Artificial Sequence
<220> FEATURE:
<223> OTHER INFORMATION: synthetic peptide

<400> SEQUENCE: 38

Met Trp Glu Tyr Ser
1               5
```

US 7,547,676 B2

ANTAGONIST PEPTIDES TO THE C5A CHEMOTACTIC FUNCTION OF VITAMIN D BINDING PROTEIN

CROSS REFERENCE TO RELATED APPLICATION

The present application claims the benefit of U.S. Provisional Application No. 60/616,105 filed Oct. 5, 2004.

GOVERNMENT INTEREST

The present invention was supported with Government support under Grant No. GM 63769 (National Institutes of Health). The Government may have certain rights in the invention.

FIELD OF THE INVENTION

The present invention relates to protein and peptide chemistry. In particular, the present invention relates to the discovery and isolation of novel peptides whose sequences coincide with regions of the Vitamin D Binding Protein (DBP). The invention is also directed to the use of these novel peptides as antagonists to the DBP-mediated biological activity.

BACKGROUND OF THE INVENTION

Vitamin D Binding protein (DBP) is a multifunctional and highly polymorphic plasma protein synthesized primarily in the liver (see White, P. et al., *Trends Endocrinol. Metabol.* 11, 320-327 (2000); Gomme, P. T. et al., *Trends Biotechnol.* 22, 340-345 (2004)). DBP is expressed as a single polypeptide chain with a molecular mass of approximately 56 kDa and circulates in plasma at 6 to 7 µM (see White, P. et al.; Gomme, P. T. et al.). Due to its extensive polymorphisms DBP initially was named the group-specific component of serum, later shortened to Gc-globulin (see Hirschfeld, J. *Acta Pathol. Microbiol. Scand.* 47, 160 (1959)). DBP is a member of the albumin (ALB), alpha-fetoprotein (AFP), and alpha-albumin/afamin (AFM) gene family and hence has the characteristic multiple disulfide-bonded, triple domain modular structure (see White, P. et al.). Besides functioning as a circulating vitamin D transport protein, it has been demonstrated that plasma DBP effectively scavenges G-actin released at sites of necrotic cell death and prevents polymerization of actin in the circulation (see White, P. et al.; Gomme, P. T. et al.). Distinct binding regions within the 458 amino acid sequence of DBP have been identified: a vitamin D sterol binding segment in the N-terminal domain (amino acids 35 to 49) and a G-actin binding region in the C-terminal domain (amino acids 373 to 403) (see Haddad, J. G. et al., *Biochemistry* 31, 7174-7181 (1992); Swamy, N. et al., *Biochemistry* 36, 7432-7436 (1997)). More recent work on the crystal structure of DBP (bound to either vitamin D3 or actin) has confirmed the vitamin D sterol binding site, but has demonstrated that actin interacts with distinct amino acid sequences in all three DBP domains (see Verboven, C. et al., *Nat. Struct. Biol.* 9, 131-136 (2002); Swamy, N. et al., *Arch. Biochem. Biophys.* 402, 14-23 (2002); Head, J. F. et al., *Biochemistry* 41, 9015-9020 (2002); Otterbein, L. R. et al., *Proc. Natl. Acad. Sci. USA* 99, 8003-8008 (2002)).

Complement C5a is a 74-amino acid peptide generated by limited proteolytic cleavage of C5 during complement activation (see Kohl, J. *Mol. Immunol.* 38, 175-187 (2001)). C5a is a very potent chemotactic factor for all leukocytes as well as several other cell types and the peptide has several other pro-inflammatory functions as well (see Kohl, J.). C5a exerts these activities by binding to its high affinity receptor (C5aR or CD88) on the plasma membrane of target cells (see Gerard, N. P. et al. *Nature.* 349, 614-617 (1991)).

Several groups have demonstrated that purified DBP can significantly enhance the neutrophil chemotactic activity (i.e., cochemotatic activity) of C5a, and its stable breakdown product C5a des Arg (see Kew, R. R. et al., *J. Clin. Invest.* 82, 364-369 (1988); Perez, H. D. et al., *J. Clin. Invest.* 82, 360-363 (1988); Petrini, M. et al., *J. Endocrinol. Invest.* 14, 405-408 (1991); Metcalf, J. P. et al., *Am. Rev. Respir. Dis.* 143, 844-849 (1991); Binder, R. et al., *Mol. Immunol.* 36, 885-892 (1999); Zwahlen, R. D. et al., *Inflammation* 14, 109-123 (1990)). In addition to neutrophils, DBP can also augment the C5a chemotactic activity for monocytes and fibroblasts (see Piquette, C. A. et al., *J. Leukoc. Biol.* 55, 349-354 (1994); Senior, R. M. et al., *J. Immunol.* 141, 3570-3574 (1988)). The chemotactic enhancing properties of DBP appear to be restricted to C5a/C5a des Arg since this protein cannot enhance the chemotactic activity of formylated peptides, IL-8, leukotriene B4 or platelet activating factor (see Kew, R. R. et al.; Perez, H. D. et al.; Binder, R. et al.; Piquette, C. A. et al.).

Surface plasmon resonance (SPR) is a powerful state-of-the-art technology that enables investigators to measure the interaction between molecules in real time. The leader in this technology is Biacore AB (Uppsala, Sweden) and the SPR applications are very often referred to using the company name. Using Biacore, the molecule of interest (ligand) is immobilized to a sensor chip. The sensor chip is placed in a flow cell and a second soluble molecule (analyte) is allowed to interact with the immobilized ligand. The strength (association/dissociation constant) and speed (on/off rate) of the molecule interaction can be calculated in real time. Theoretically, Biacore can be used to measure cell binding to an immobilized ligand, however, very little information is available concerning this type of application.

Undifferentiated U937 cells stably transfected with the C5a receptor (U937-C5aR cells) are a good model system to study C5a-mediated cell movement and the chemotactic enhancing effect of DBP. However, the effect of DBP on C5a-mediated increase in intracellular calcium concentrations has not been determined.

SUMMARY OF THE INVENTION

The present invention is directed to vitamin D binding protein (DBP) antagonist peptides. Novel DBP antagonist peptides derived from or corresponding to the DBP N-terminal Domain I have been isolated and synthesized. These peptides possess DBP antagonist properties including the ability to block, interfere with or prevent DBP from enhancing the C5a /C5a des Arg-mediated chemotaxis and $Ca^{2+}$ influx in differentiated HL-60 cells. The present invention recognizes a novel DBP binding/signaling complex comprising annexin A2, CD36, CD47 and CD44 that mediates the cochemotactic signal from DBP (Trujillo and Kew, *J. Immunol.* 173:4130, 2004; McVoy and Kew, *J. Immunol.* 175:4754, 2005; Abstract, 10th*European Meeting on Complement in Human Disease*, Heidelberg, Germany, Sep. 11, 2005).

In one aspect, the peptides of the present invention have an amino acid sequence that corresponds with the N-terminal domain I of human, rat, mouse, rabbit or turtle DBP (residues 130-149), including variations thereof.

In another aspect, the peptides of the present invention have an amino acid sequence that corresponds with the N-terminal domain I of human DBP (residues 130-149), including variations thereof.

Homologs, analogs and fragments of these peptides are also contemplated by the present invention as DBP peptide antagonists which block, interfere with or prevent the DBP enhancement of C5a /C5a des Arg chemotactic activity.

The present invention also provides compositions for treating C5a /C5a des Arg-mediated disorders such as immunoinflammatory disorders. The present invention provides specific compositions containing at least one DBP antagonist peptide which inhibits, suppresses or causes the cessation of at least one DBP-mediated biological activity in a mammal including humans.

The present invention further provides a method for treating C5a /C5a des Arg-mediated disorders, such as immunoinflammatory disorders, by administering to a subject in need of such treatment a therapeutic effective amount of the peptides or composition of the present invention.

Nucleic acid molecules coding for any of the above DBP antagonist peptides of the present invention, expression vectors which include any of such nucleic acid molecules, as well as related host cells containing such nucleotide sequences or vectors, are also contemplated by the present invention.

Still another aspect of the present invention is directed to antibodies raised against the DBP antagonist peptides of the present invention. The antibodies of the present invention are raised against those DBP antagonist peptides whose sequences coincide with the corresponding sequences of a vertebrate DBP protein. Both, polyclonal antibodies and monoclonal antibodies, are contemplated by the present invention.

The present invention is further directed to antagonist peptides or antibodies against CD36, CD47, CD44 and/or annexin A2 and a method for treating C5a /C5a des Arg-mediated disorders, such as immunoinflammatory disorders, by administering to a subject in need of such treatment a therapeutic effective amount of the antagonist peptides or antibodies against CD36, CD47, CD44 and/or annexin A2.

These and other embodiments of the invention will be readily apparent to those of ordinary skill in view of the disclosure herein.

BRIEF DESCRIPTION OF DRAWINGS

FIG. 1 shows the effect of DBP on C5a-mediated responses in differentiated HL-60 cells. HL-60 cells were differentiated using 250 μM $bt_2cAMP$ for 48 hours. Panel A: Cells ($6\times10^6$/ml) were resuspended in chemotaxis buffer allowed to respond to 25, 50, 100, or 200 pM C5a with or without 50 nM DBP for 60 minutes at 37° C. Numbers represent net cell movement in 60 min, mean±SEM of 3 to 5 experiments. Panel B: Cells loaded with Fluo-3 AM dye were resuspended in HBSS +1% BSA at $5\times10^6$/ml with or without 50 nM DBP and then incubated at room temperature for 30 min. Increase in intracellular calcium after stimulation with 25, 50, 100 or 200 pM C5a was measured at excitation of 505 nm and emission of 525 nm. Data are expressed mean±SEM of the nM change in intracellular $Ca^{2+}$ level of 3 to 5 separate experiments. Asterisks denote that the indicated sample is significantly greater (p<0.01) than the corresponding control value.

FIG. 2 shows the structural analysis of full-length and truncated recombinant DBP. Panel A: SDS-PAGE analysis, Lane 1 from left: GST with full-length reDBP (1-458), GST with domains I & II (1-378), GST with domains II & III (192-458), GST with domain I (1-191), GST with domain II (192-378). GST alone is approximately 28 kDa. Positions of molecular weight markers are shown on the right of panel. Panel B: Western blot analysis of expressed recombinant DBP (after thrombin-cleavage to remove the GST). 250 ng of each recombinant DBP were separated on 10% SDS-PAGE and immunoblotted using polyclonal anti-DBP.

FIG. 3 provides the analysis of vitamin D sterol binding to reDBP. Competitive $^3H$-5(OH)$D_3$ binding assay of natural DBP and reDBPs. Solutions containing natural DBP or reDBPs (200 ng), $^3H$-25-OH-$D_3$ (0.1 pmol), unlabeled 25-OH-$D_3$ (0.5-64 pmol) in a total volume of 10 μl was added to 490 μl assay buffer (50 mM Tris-HCL pH 8.3, 150 mM NaCl, 1.5 mM EDTA, 0.1% Triton X-100) and incubated at 4° C. for 20 hours. Samples were then treated with 100 μl of ice-cold 2.5% Dextran-coated charcoal to remove free vitamin D and then were separated by centrifugation at 5000× g at 4° C. Supernatants were mixed with scintillation cocktail and counted for radioactivity. Data are presented as the ratio of radiolabel bound with unlabeled competitor (B) divided by radiolabel bound without competitor (B0). Results are representative of three separate experiments.

FIG. 4 shows the effect of reDBP on C5a-mediated responses in differentiated HL-60 cells. HL-60 cells were differentiated using 250 μM $bt_2cAMP$ for 48 hours. Panel A: Cells ($6\times10^6$/ml) were resuspended in chemotaxis buffer allowed to respond to 100 pM C5a alone (Control) or C5a plus 50 nM of each indicated DBP for 60 minutes at 37° C. Numbers represent net cell movement in 60 min, mean±SEM of 3 to 5 experiments. Panel B: Cells loaded with Fluo-3 AM dye were resuspended in HBSS+1% BSA at $5\times10^6$/ml with or without 50 nM of the indicated DBP and then incubated at room temperature for 30 min. Increase in intracellular calcium after stimulation with 100 pM C5a was then measured. Data are expressed as the maximal nM change in the intracellular $Ca^{2+}$ level. Results are the mean±SEM of 3 separate experiments. Asterisks denote that sample is significantly greater (p <0.01) than control value.

FIG. 5 provides the structural analysis of truncated versions of DBP domain I. Panel A: SDS-PAGE analysis, Lane 1 to 4 from left: GST with DI (1-112), GST with DI (1-125), GST with DI (1-150), GST with DI (1-175). Positions of molecular weight markers are shown on the right of panel. Panel B: Western blot analysis of expressed recombinant DBP (after thrombin-cleavage to removed the GST). 250 ng of domain I truncations were separated on 10% SDS-PAGE and immunoblotted using polyclonal anti-DBP.

FIG. 6 shows the effect of truncated reDBP of domain I on C5a-mediated responses in differentiated HL-60 cells. HL-60 cells were differentiated using 250 μM $bt_2cAMP$ for 48 hours. Panel A: Cells ($6\times10^6$/ml) were resuspended in chemotaxis buffer allowed to respond to 100 pM C5a alone (Control) or C5a plus 50 nM of each indicated DBP for 60 minutes at 37° C. Numbers represent net cell movement in 60 min, mean±SEM of 3 to 5 experiments. Panel B: Cells loaded with Fluo-3 AM dye were resuspended in HBSS +1% BSA at $5\times10^6$ /ml with or without 50 nM of the indicated DBP and then incubated at room temperature for 30 min. Increase in intracellular calcium after stimulation with 100 pM C5a was then measured. Data are expressed as the maximal nM change in the intracellular $Ca^{2+}$ level. Results are the mean±SEM of 3 separate experiments. Asterisks denote that the sample is significantly greater (p<0.01) than control value.

FIG. 7 shows the effect of DBP domain I peptides on C5a-mediated chemotaxis. Cells ($6\times10^6$/ml) were resuspended in chemotaxis buffer and treated either with chemotaxis buffer (control), 1 μM of peptide 1 (130-152), or 1 μM of peptide 2 (150-172) for 30 min at room temperature. The chemotactic response of differentiated HL-60 cells to 100 pM C5a alone, C5a plus 50 nM full-length natural DBP or 1% zymosan-activated serum (ZAS) was measured for 60 minutes at 37° C. Numbers represent net cell movement in 60 min, mean±SEM of 3 experiments. Asterisks denote that the indicated sample is significantly less (p<0.01) than the corresponding control value.

Figure 8:
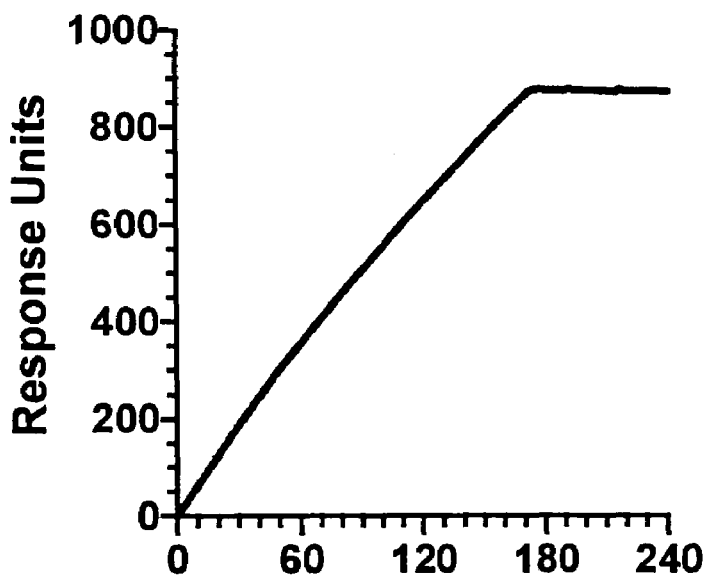
Figure 8:
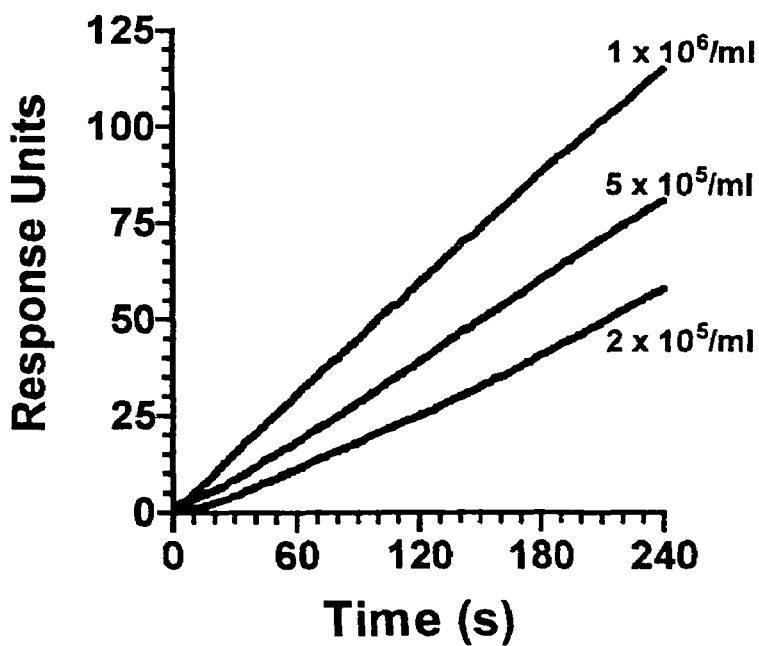

FIG. 8A and FIG. 8B show immobilization of DBP on a Biacore surface plasmon resonance sensor chip CM5. Purified DBP in HBSS (5 μM) was coupled to the sensor chip. Coupling was detected using 5 μg/ml affinity-purified anti-DBP (FIG. 8A). Different concentrations of U937-C5aR cells in HBSS were injected into the flow cell and allowed to interact with the immobilized DBP (FIG. 8B). Data is expressed as response units of the molecular interaction on the sensor chip.

Figure 9:
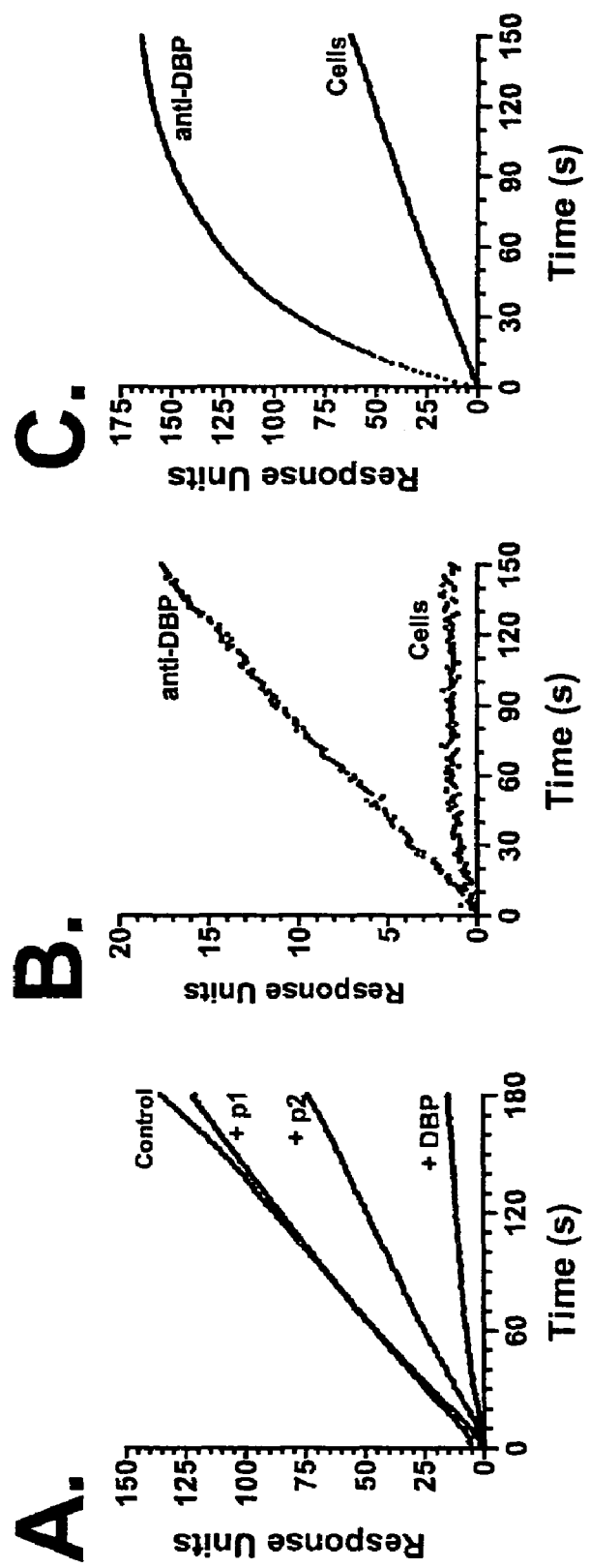

FIGS. 9A to 9C show the effect of pretreating U937-C5aR cells with purified DBP or DBP peptides on the binding to DBP immobilized on a Biacore sensor chip. FIG. 9A: $10^6$ cells/ml in HBSS were not treated (control), pretreated with 50 nM DBP, 0.5 μM DBP peptide 1 (p1) or DBP peptide 2 (p2). FIG. 9B: DBP peptide 1 immobilized to the Biacore sensor chip. FIG. 9C: DBP peptide 2 immobilized to the Biacore sensor chip. Data is expressed as response units of the molecular interaction on the sensor chip.

Figure 10:
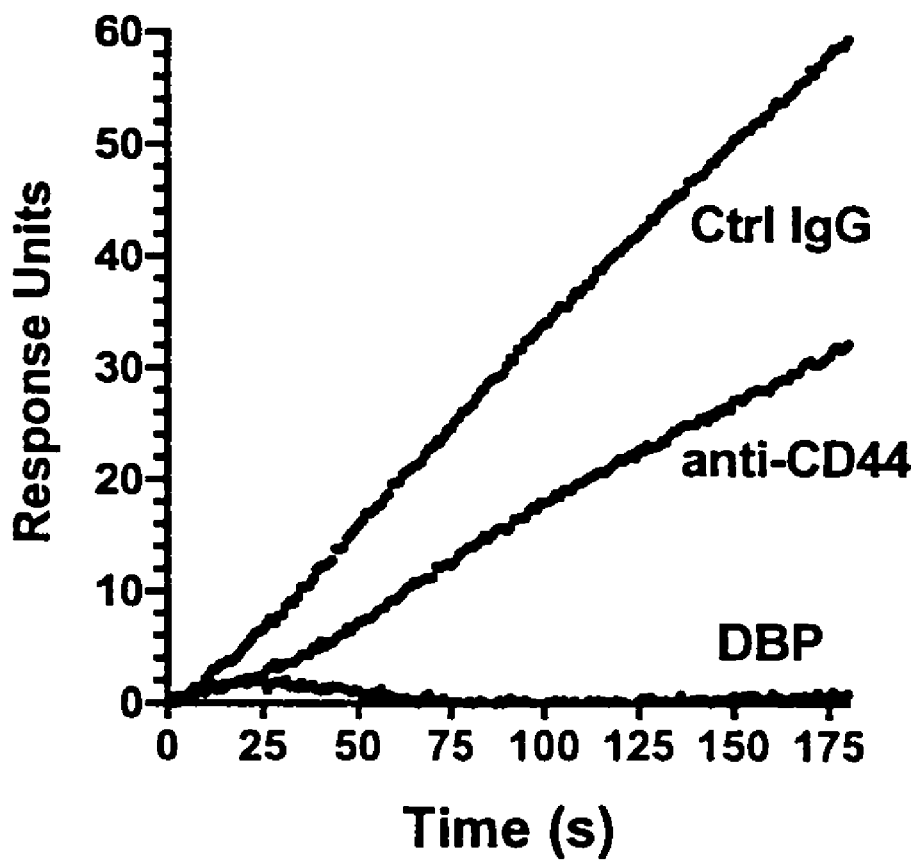

FIG. 10 demonstrates that anti-CD44 partially blocks U937-C5aR binding to DBP immobilized on a Biacore sensor chip. U937-C5aR cells ($10^6$ cells/ml in HBSS) were pretreated with a 25 μg/ml control IgG, 50 nM purified DBP or 25 μg/ml affinity-purified anti-CD44 and then allowed to interact with DBP immobilized on a Biacore sensor chip. Data is expressed as response units of the molecular interaction on the sensor chip.

Figure 11:
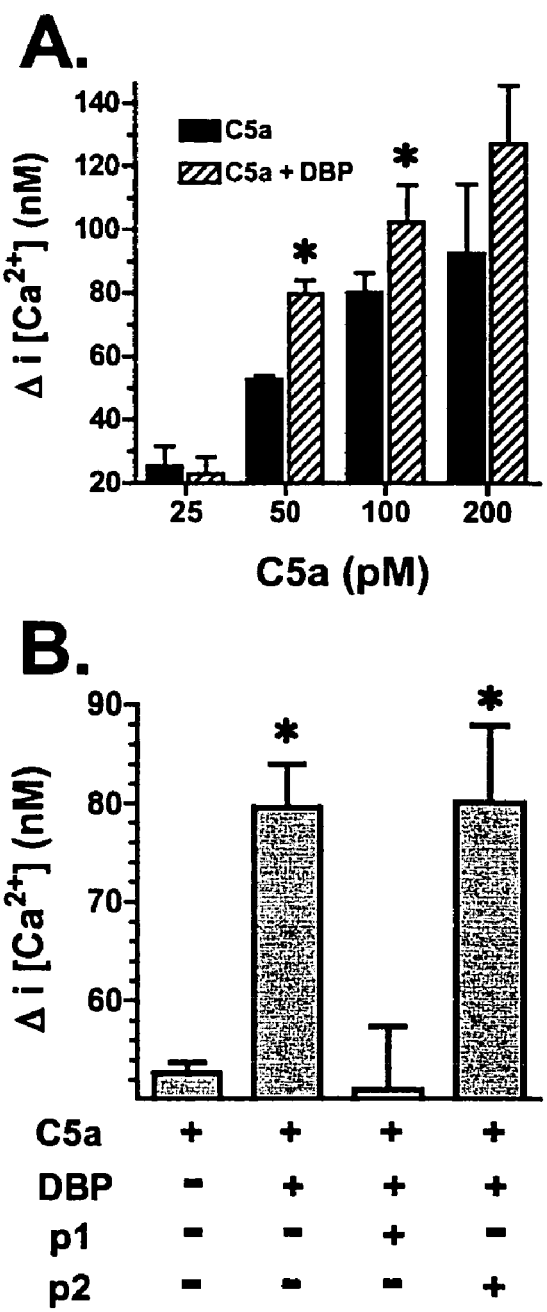

FIG. 11A and FIG. 11B show the effect of DBP on C5a-induced intracellular calcium mobilization in U937-C5aR cells. U937-C5aR cells ($10^7$ cells/ml) were resuspended in HBSS-1% BSA containing 2 μM Fluo-3 AM and incubated at 37° C. for 40 minutes. Cells incubated without the dye were used as a control to measure autofluorescence (Fmin). Following the dye uptake, cells were washed twice then suspended at $5\times10^6$ cells/ml in HBSS containing 1% BSA. For the pretreatment experiments, cells were incubated for 30 min at 22° C. with 50 nM DBP or 0.5 μM DBP peptide 1 (p1). For each measurement, 400 μl of cell suspension was added to a cuvette and stimulated with the indicated concentration of C5a (FIG. 11A) or 0.1 nM C5a (FIG. 11B). Fluorescence was then measured immediately using a Perkin-Elmer LS-5 fluorometer at 505 nm excitation, 526 nm emission for Fluo-3 AM. Fmax was measured by treating labeled cells with 60 μM digitonin. Intracellular free calcium concentrations were calculated using the following formula: $(Ca^{2+})=K_d (F-Fmin)/(Fmax-F)$, where $K_d=325$ nM for Fluo-3 according to manufacturer (Molecular Probes). Data are presented as mean±SEM (n=4-6) of the increase in intracellular calcium concentration. Asterisk indicates value is significantly higher (p<0.05) than the corresponding value not treated with DBP.

Figure 12:
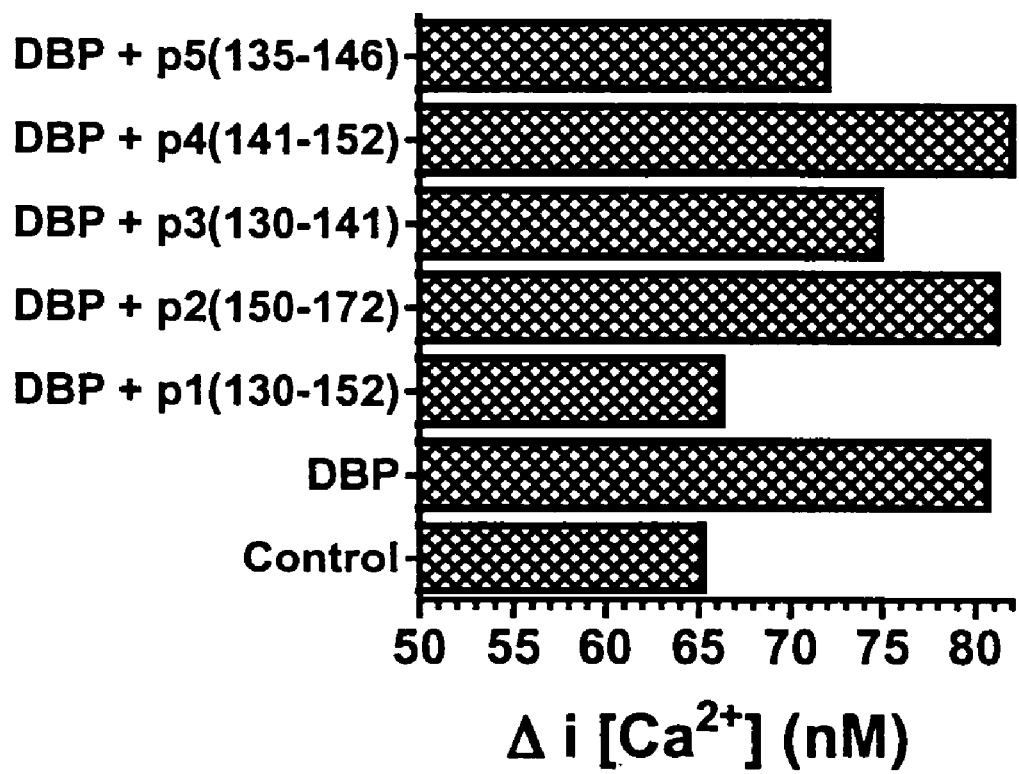

FIG. 12 demonstrates the effect of DBP peptides on C5a-induced intracellular calcium mobilization in U937-C5aR cells. U937-C5aR cells ($10^7$ cells/ml) were resuspended in HBSS-1% BSA containing 2 μM Fluo-3 AM and incubated at 37° C. for 40 minutes. Cells incubated without the dye were used as a control to measure autofluorescence (Fmin). Following the dye uptake, cells were washed twice then suspended at $5\times10^6$ cells/ml in HBSS containing 1% BSA. Cells were incubated for 30 min at 22° C. with either 50 nM DBP or 0.5 μM DBP peptide. For each measurement, 400 μl of cell suspension was added to a cuvette and stimulated with 0.1 nM purified C5a. Fluorescence was then measured immediately using a Perkin-Elmer LS-5 fluorometer at 505 nm excitation, 526 nm emission for Fluo-3 AM. Fmax was measured by treating labeled cells with 60 μM digitonin. Intracellular free calcium concentrations were calculated using the following formula: $(Ca2+)=Kd (F-Fmin)/(Fmax-F)$, where Kd=325 nM for Fluo-3 according to manufacturer (Molecular Probes)

Figure 13:
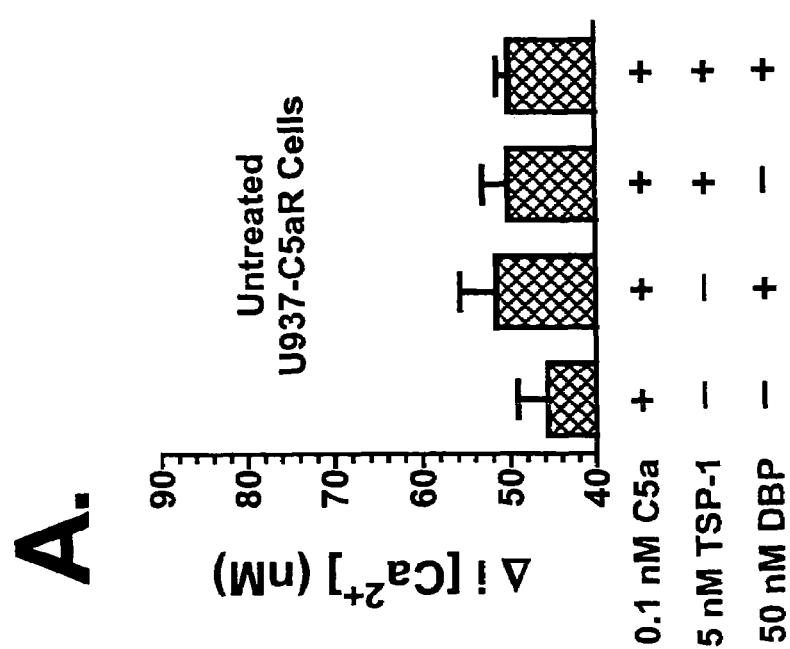

FIG. 13A and FIG. 13B show the effect of DBP and TSP-1 on C5a-induced intracellular calcium mobilization in U937-C5aR cells. U937-C5aR cells ($10^7$ cells/ml) were resuspended in HBSS-1% BSA containing 2 μM Fluo-3 AM and incubated at 37° C. for 40 minutes. Cells incubated without the dye were used as a control to measure autofluorescence (Fmin). Following the dye uptake, cells were washed twice then suspended at $5\times10^6$ cells/ml in HBSS containing 1% BSA. For the pretreatment experiments, cells were incubated for 30 min at 22° C. with either 0.5 nM TSP-1 or 50 nM DBP. For each measurement, 400 μl of cell suspension was added to a cuvette and stimulated with 0.1 nM purified C5a, C5a+0.5 nM TSP-1 or C5a+50 nM DBP at 22° C. Fluorescence was then measured immediately using a Perkin-Elmer LS-5 fluorometer at 505 nm excitation, 526 nm emission for Fluo-3 AM. Fmax was measured by treating labeled cells with 60 μM digitonin. Intracellular free calcium concentrations were calculated using the following formula: $(Ca2+)=Kd (F-Fmin)/(Fmax-F)$, where Kd=325 nM for Fluo-3 according to manufacturer (Molecular Probes).

Figure 14:
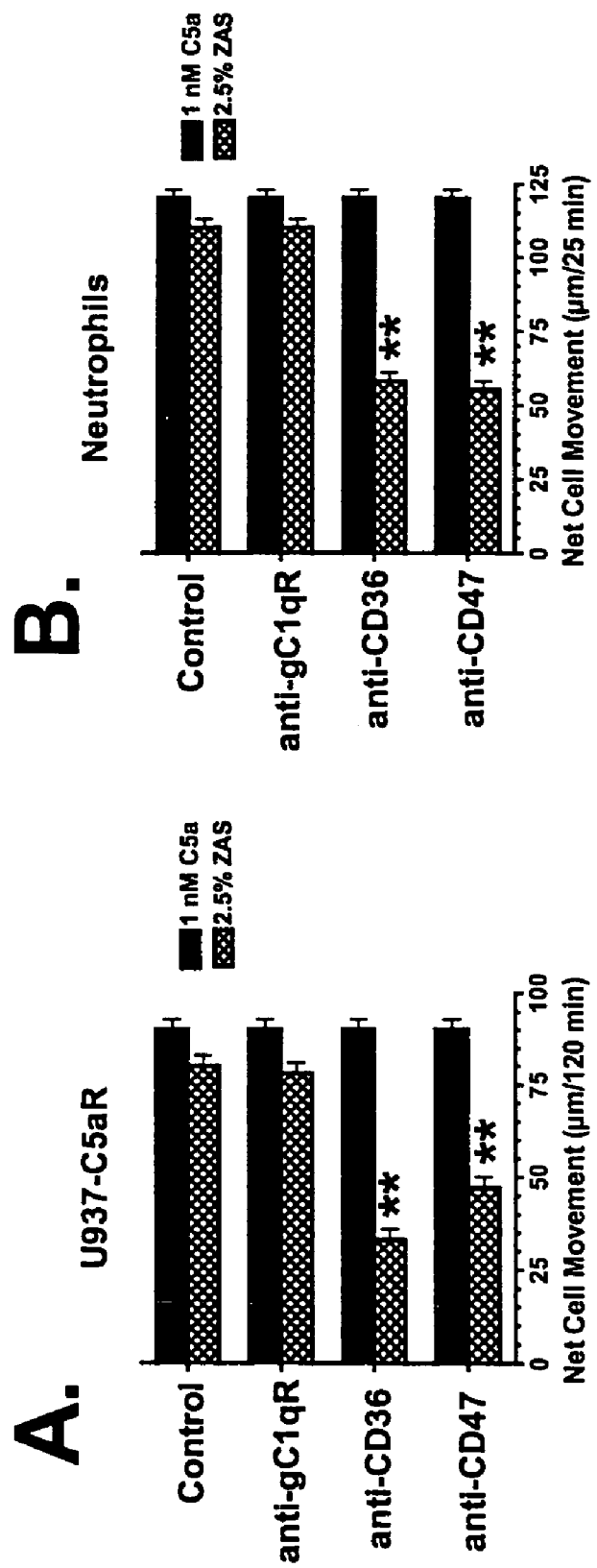

FIG. 14A and FIG. 14B show that anti-CD36 and anti-CD47 treatment inhibit neutrophil and U937-C5aR cell movement to complement-activated serum. Neutrophils ($4\times10^6$/ml) or U937-C5aR cells ($6\times10^6$/ml) in chemotaxis buffer were treated for 15 min at 22° C. with 20 μg/ml of anti-CD36, anti-CD47 or anti-gC1qR. Cells were then allowed to respond to either 2.5% complement-activated serum (ZAS) or 1 nM purified C5a for 120 min (FIG. 14A. U937-C5aR cells) or 25 min (Panel B. neutrophils) at 37° C. Numbers represent mean±SEM, n=4. Asterisks denote that cell movement was significantly less (p<0.01) than to the untreated control.

Figure 15:
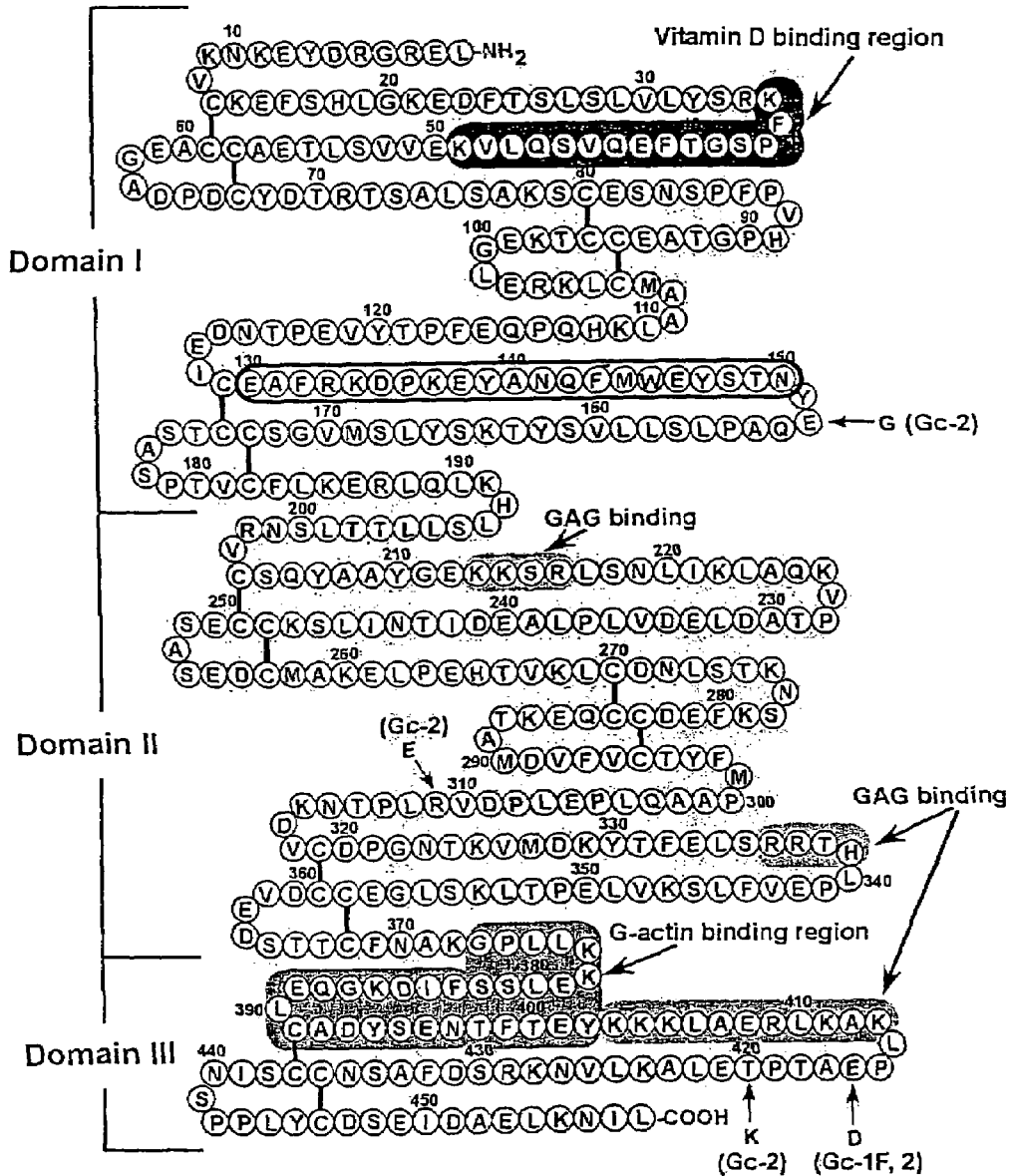

FIG. 15 depicts primary structure of human DBP, showing Domains I-III and ligand binding sites.

DETAILED DESCRIPTION OF THE INVENTION

The present invention is directed to Vitamin D Binding Protein (DBP) antagonist peptides. In one embodiment, the peptides of the present invention have an amino acid sequence that corresponds with the N-terminal domain I of human, rat, mouse, rabbit or turtle DBP (residues 130-149), including variations thereof.

In the present invention, full-length and truncated versions of DBP (Gc-2 allele) were expressed in *E. coli* using the GST fusion protein expression system. Structure of the expressed proteins was confirmed by SDS-PAGE and immunoblotting, while protein function was verified by quantitating the binding of $^3$H-vitamin D. Dibutyryl cAMP-differentiated HL-60 cells were utilized to test purified natural DBP (nDBP) and recombinant expressed DBP (reDBP) for their ability to enhance chemotaxis and intracellular Ca$^{2+}$ flux to C5a. Natural and full-length reDBP (458 amino acid residues) as well as truncated reDBPs that contained the N-terminal domain I (domain I & II, residues 1-378; domain I, residues 1-191) significantly enhanced both cell movement and intracellular Ca$^{2+}$ concentrations in response to C5a.

According to the present invention, the interaction of an immobilized ligand, e.g., immobilized DBP, binding to cells can be measure by any established technology available in the art, e.g., by surface plasmon resonance (SPR) or Biacore technology. For example, in the present invention, the binding of U937-C5aR cells to immobilized DBP were examined by Biacore technology, the result of which is used to further determine if the DBP peptides generated in the present invention can alter the interaction U937-C5aR cells and DBP. FIG. 8A shows that purified DBP was successfully immobilized to a Biacore CM5 sensor chip as evidenced by the dramatic increase in the response units when affinity-purified anti-DBP was injected into the flow cell. FIG. 8B shows the effect of various U937-C5aR cell concentrations on the binding to immobilized DBP, note the concentration dependent increase in binding. These experiments clearly demonstrate that Biacore technology can measure DBP-cell interactions. FIG. 9A shows U937-C5aR cell binding to the DBP chip (control) and this interaction is almost completely blocked if cells are preincubated with soluble DBP (+DBP) before they are injected into the flow cell. Moreover, pretreatment of cells with DBP peptide 1 (+p1) had no effect on cell binding to the fulllength protein but peptide 2 (+p2) inhibited cell binding by almost 50%. To investigate further the effect of DBP peptides on cell binding, peptide 1 (FIG. 9B) and peptide 2 (FIG. 9C) were immobilized to Biacore sensor chips. FIGS. 9B and 9C demonstrate that the peptides were successfully immobilized as evidenced by the increase in response units when anti-DBP was injected into the flow cell. U937-C5aR cells do not bind to immobilized peptide 1 (FIG. 9B) but do bind peptide 2 (FIG. 9C) confirming the results from FIG. 9A. Finally, the present invention also identifies that CD44 on the cell surface binds DBP and can, in part, mediate the C5a chemotactic cofactor effect of DBP (McVoy and Kew, J. Immunol. 175: 4754, 2005). Therefore, using Biacore technology the present invention addresses the effect of blocking CD44 on U937-C5aR binding to immobilized DBP (FIG. 10). In the present invention, U937-C5aR cells were pretreated with either an irrelevant goat IgG (negative control), purified soluble DBP (positive control) or affinity-purified goat anti-CD44. FIG. 10 demonstrates that DBP completely blocks binding whereas anti-CD44 inhibits binding by about 50%. These Biacore experiments have provided a powerful quantitative tool to investigate the cell binding region on DBP and examine the effects on DBP peptides on this interaction.

In the present invention, progressive truncation of DBP domain I localized the chemotactic enhancing region between residues 126-175. Overlapping peptides corresponding to this region were synthesized and results indicated that a 20 amino acid sequence (residues 130-149, EAFRKD-PKEYANQFMWEYST (SEQ ID NO: 1)) in domain I of DBP is essential for its C5a chemotactic cofactor function.

According to the present invention, DBP can enhance the C5a signal. For example, in the present invention, pretreatment of U937-C5aR cells with DBP significantly augments the C5a-induced increase in intracellular calcium (FIG. 11A), which is an indicator that DBP enhances the C5a signal. The present inventors have also shown that DBP peptide 1 (amino acids 130-152, SEQ ID NO: 3) completely blocked the chemotactic enhancing effect of DBP, using both purified proteins and complement-activated serum, in differentiated HL-60 cells (see also, Zhang & Kew, J. Biol. Chem. 279: 53282, 2004). FIG. 11B shows that DBP peptide 1 also completely blocks the DBP-induced increase in the C5a calcium signal, further supporting the observation of chemotactic enhancing effect of DBP and extending this observation to a new cellular assay (calcium flux assay). The chemotactic cofactor region in DBP (amino acid # 130-149, SEQ ID NO: 1) was determined using two overlapping peptides: peptide 1 (130-152, SEQ ID NO: 3) and peptide 2 (150-172, SEQ ID NO: 4).

According to the present invention, an antagonist peptide of DBP is at least about 4 amino acid residues in length, preferably, at least about 6 amino acid residues in length, more preferably, at least about 11 amino acid residues in length, more preferably, at least about 14 amino acid residues in length, and most preferably, at least about 20 amino acid residues in length. These antagonist peptides can also function to block the DBP-enhanced C5a calcium signal. For example, in addition to peptide 1, which possesses the ability to block chemotaxis to C5a+DBP, three shorter peptides were generated in the present invention: peptide 3 (# 130-141, SEQ ID NO: 8), peptide 4 (#141-152, SEQ ID NO: 9) and peptide 5 (#135-146, SEQ ID NO: 10). FIG. 12 shows that peptides 3 and 5 can partially block the DBP-enhanced C5a calcium signal.

By "DBP antagonist" is meant any molecule, preferably, a peptide, that inhibits, suppresses or causes the cessation at least one DBP-mediated biological activity by, e.g., interfering with, blocking or otherwise preventing DBP from enhancing C5a/C5a des Arg chemotaxis of leukocytes. DBP antagonists can be useful in the treatment of immunoinflammatory responses in which C5a/C5a des Arg participates.

As used herein, "C5a" refers to the 74-amino acid peptide generated by limited proteolytic cleavage of C5 during complement activation (Kohl, J. Mol. Immunol. 38, 175-187 (2001)). By "C5a des Arg" is meant the stable breakdown product of C5a (see Kew, R. R. et al., J. Clin. Invest. 82, 364-369 (1988); Perez, H. D. et al., J. Clin. Invest. 82, 360-363 (1988); Petrini, M. et al., J. Endocrinol. Invest. 14, 405-408 (1991); Metcalf, J. P. et al., Am. Rev. Respir. Dis. 143, 844-849 (1991); Binder, R. et al., Mol. Immunol. 36, 885-892 (1999); Zwahlen, R. D. et al., Inflammation 14, 109-123 (1990)).

By "C5a/C5a des Arg" is meant either C5a or C5a des Arg.

The term "peptide" refers to a linear series of amino acid residues linked to one another by peptide bonds between the alpha-amino and carboxy groups of adjacent amino acid residues. The term "synthetic peptide" is intended to refer to a chemically derived chain of amino acid residues linked together by peptide bonds. The term "synthetic peptide" is also intended to refer to recombinantly produced peptides in accordance with the present invention.

The sequences of peptides of the present invention are derived from and/or correspond to the amino acid sequence of the human DBP N-terminal Domain I. See FIG. 15. However, homologous peptides derived from rat, mouse, rabbit, chicken, turtle and other vertebrates are also encompassed by the invention. As it is shown in Table I, there is substantial homology among the sequences corresponding to residues 130 to 149 of the DBP N-terminal Domain I in human, rat, mouse, rabbit, chicken and turtle.

TABLE I

Sequence Homology/Identity for residues 130-149 of DBP N-terminal Domain I in human, mouse, rat, rabbit, chicken and turtle. An asterisk (*) indicates the identical residue as the residue of the corresponding position in the human sequence.

| Species | Sequence (residues 130-149 of DBP N-terminal Domain I) | Homology/Identity (%) |
|---|---|---|
| Human | EAFRKDPKEYANQFMWEYST | (SEQ ID NO: 1) |
| Mouse | ********GF*DLY*S | 70 |
| Rat | ********GF*DLF*S | 70 |
| Rabbit | **QM*F*DK*LY***S | 60 |
| Chicken | *K**DF*DR*LH*** | 60 |
| Turtle | *K*QGF**R*TY***I | 60 |

According to the present invention, preferred DBP antagonists include peptides (referred to herein as "DBP antagonist peptides") and antibodies.

By "DBP biological activity" as used herein is meant the ability of DBP to augment or enhance the C5a/C5a des Arg chemotactic activity for neutrophils, monocytes, fibroblasts and any other cell expressing the C5a/C5a des Arg membrane receptor.

By "homologs" is meant the corresponding peptides from DBP proteins of other vertebrate species substantially homologous at the overall protein (i.e., mature protein) level to human, rat, mouse, rabbit, chicken or turtle DBP, so long as such homologous peptides retain the DBP antagonist activity.

By "analogs" is meant peptides that differ by one or more amino acids alterations, which alterations, e.g., substitutions, additions or deletions of amino acid residues, do not abolish the DBP antagonist properties of the relevant peptides.

According to the present invention, a DBP antagonist peptide is preferably at least about four amino acids in length, more preferably at least about six amino acids in length, even more preferably at least about nineteen amino acids in length, and most preferably at least about twenty amino acids in length. More specifically, the present invention provides DBP antagonist peptides which substantially correspond to sequences found in the N-terminal Domain I of DBP. An example of a suitable peptide include the sequence EAFRKDPKEYANQFMWEYST (SEQ ID NO:1), corresponding to approximately residues 130 to 149 of the N-terminal Domain I of DBP.

Thus, an analog may comprise a peptide having a substantially identical amino acid sequence to a peptide provided herein and in which one or more amino acid residues have been conservatively or non-conservatively substituted. Examples of a conservative substitution include the substitution of a hydrophobic residue such as isoleucine, valine, leucine or methionine for another. Likewise, the present invention contemplates the substitution of one aromatic residue such as phenylalanine, tryptophan or tyrosine for another. The substitution of a polar residue such as lysine, arginine, glutamine or asparagine for another or the substitution of a polar residue such as aspartate, glutamate, glutamine or asparagine for another is also contemplated. Additionally, the present invention contemplates the substitution of a non-polar aliphatic residue such as between glycine and alanine, or a polar aliphatic residue such as between serine and threonine. Examples of non-conservative substitutions include the substitution of a non-polar residue e.g., isoleucine, valine, leucine, alanine or methionine, for a polar residue e.g., glutamine, glutamate, lysine, and/or a polar residue for a non-polar residue.

The phrase "conservative substitution" also includes the use of chemically derivatized residues in place of a non-derivatized residues as long as the peptide retains the requisite DBP antagonist activity. The antagonist activity can be measured by the ability of the peptide to block the DBP enhancement of C5a /C5a des Arg chemotactic activity. Analogs also include the presence of additional amino acids or the deletion of one or more amino acids which do not affect the DBP antagonist properties of the relevant peptides. For example, analogs of the subject peptides can contain an N- or C-terminal cysteine, by which if desired, the peptide may be covalently attached to a carrier protein, e.g., albumin. Such attachment, it is believed, will minimize clearing of the peptide from the blood and also prevent proteolysis of the peptides. In addition, for purposes of the present invention, peptides containing D-amino acids in place of L-amino acids are also included in the term "conservative substitution." The presence of such D-isomers can help minimize proteolytic activity and clearing of the peptide.

A preferred DBP antagonist peptide of the present invention is a twenty-residue length peptide having the sequence E-A-F-$Xaa_1$-$Xaa_2$-D-P-$Xaa_3$-$Xaa_4$-$Xaa_5$-A-$Xaa_6$-$Xaa_7$-F-$Xaa_8$-$Xaa_9$-E-Y-S-$Xaa_{10}$ (SEQ ID NO:2), wherein $Xaa_1$, $Xaa_2$, $Xaa_3$, $Xaa_4$, $Xaa_5$, $Xaa_6$, $Xaa_7$, $Xaa_8$, $Xaa_9$, $Xaa_{10}$ can be any amino acid which includes:

A=Ala=Alanine
R=Arg=Arginine
N=Asn=Asparagine
D=Asp=Aspartate
B=Asx=Asparagine or Aspartate
C=Cys=Cysteine
Q=Gln=Glutamine
E=Glu=Glutamate
Z=Glx=Glutamine or Glutamate
G=Gly=Glycine
H=His=Histidine
I=Ile=Isoleucine
L=Leu=Leucine
K=Lys=Lysine
F=Phe=Phenylalanine
P=Pro=Proline
S=Ser=Serine
T=Thr=Threonine
W=Trp=Tryptophan
Y=Tyr=Tyrosine
V=Val=Valine Preferably, $Xaa_1$, $Xaa_2$, $Xaa_3$, $Xaa_4$, $Xaa_5$, $Xaa_6$, $Xaa_7$, $Xaa_8$, $Xaa_9$, $Xaa_{10}$ are those amino acids that are homologs of the native residues found in the human DBP N-terminal Domain I.

More preferably, $Xaa_1$, $Xaa_2$, $Xaa_3$, $Xaa_4$, $Xaa_5$, $Xaa_6$, $Xaa_7$, $Xaa_8$, $Xaa_9$, $Xaa_{10}$ are those amino acids found in the native sequence of a vertebrate DBP. For Example $Xaa_1$ can be R or K (human, chicken, turtle), $Xaa_2$ can be K or Q (human, rabbit), $Xaa_3$ can be K or M (human, rabbit), $Xaa_4$ can be E, G or D human, rat, mouse, chicken, turtle), $Xaa_5$ can be Y or F (human, rat, mouse, rabbit, chicken, turtle), $Xaa_6$ can be N or D (human, rat, mouse, rabbit and chicken), $Xaa_7$ can be Q, K or R (human, rabbit, chicken, turtle), $Xaa_8$ can be M, L or T (human, rat, mouse, rabbit, chicken, turtle), $Xaa_9$ can be W, F, Y or H (human, rat, mouse, rabbit, chicken, turtle), and $Xaa_{10}$ can be T, S or I (human, rat, mouse, rabbit, turtle).

Even more preferably, E-A-F-$Xaa_1$-$Xaa_2$-D-P-$Xaa_3$-$Xaa_4$-$Xaa_5$-A-$Xaa_6$-$Xaa_7$-F-$Xaa_8$-$Xaa_9$-E-Y-S-$Xaa_{10}$ (SEQ ID NO:2) is a twenty-residue length peptide identical to the amino acid residues 130-149 of the native human DBP N-terminal Domain I. An example of such twenty-residue length peptide includes the sequence EAFRKDPKEYANQFM-WEYST (SEQ ID NO:1). Homologs and analogs of this twenty-residue length peptide are also contemplated by the present invention, as long as such homologs and analogs maintain DBP antagonist properties.

Further, according to the present invention a DBP antagonist peptide can be longer or shorter than a twenty-residue length peptide, as long as the antagonist peptide encompasses all or part of SEQ ID NO:1 or SEQ ID NO:2 and maintains DBP antagonist activity. Preferably, the DBP antagonist peptide is at least about 4 residues in length, preferably, at least about 6 residues in length, more preferably at least about 11 residues in length, even more preferably at least about 14 residues in length, and most preferably at least 20 residues in length.

Preferred DBP antagonist peptides include those having sequences that substantially correspond with the native sequence of residues 130 to 149 of the human DBP N-terminal Domain I (SEQ ID NO:1), or the corresponding position of other vertebrate DBP molecules (SEQ ID NO:2), or the homologs or analogs of SEQ ID NO:1 and SEQ ID NO:2.

As used herein, the term "substantially correspond" is meant to the degree of amino acid homology of at least about 50% homology/identity, preferably at least about 60% homology, more preferably at least about 70% homology/identity, even more preferably at least about 75% homology/identity, and most preferably at least about 90% homology/identity, which degree is the similarity index calculated using the Lipman-Pearson Protein Alignment Program with the following choice of parameters: Ktuple=2, Gap Penalty=4, and Gap Length Penalty=12.

The term "fragment" refers to any subject peptide having an amino acid sequence shorter or longer than that of the peptide depicted in SEQ ID NO:1 or SEQ ID NO:2, wherein the fragment retains the DBP antagonist activity. Contemplated fragments include but are not limited to:

| | |
|---|---|
| EAFRKDPKEYANQFMWEYSTNYG | (SEQ ID NO: 3) |
| NYGQAPLSLLVSYTKSYLSMVGS | (SEQ ID NO: 4) |
| EAFRKDPKEYANQFMWEYS | (SEQ ID NO: 5) |
| EAFRKDPKEYANQFM | (SEQ ID NO: 6) |
| DPKEYANQFMWEYST | (SEQ ID NO: 7) |
| EAFRKDPKEYAN | (SEQ ID NO: 8) |
| DPKEYANQFMWE | (SEQ ID NO: 9) |
| NQFMWEYSTNYG | (SEQ ID NO: 10) |
| YANQFMWEYST | (SEQ ID NO: 11) |
| EAFRKDPKEY | (SEQ ID NO: 12) |
| ANQFMWEYST | (SEQ ID NO: 13) |
| DPKEYANQFM | (SEQ ID NO: 14) |

-continued

| | |
|---|---|
| NQFMWEYST | (SEQ ID NO: 15) |
| NQFMWEYS | (SEQ ID NO: 16) |
| QFMWEYST | (SEQ ID NO: 17) |
| NQFMWEY | (SEQ ID NO: 18) |
| QFMWEYS | (SEQ ID NO: 19) |
| FMWEYST | (SEQ ID NO: 20) |
| EAFRKD | (SEQ ID NO: 21) |
| KEYANQ | (SEQ ID NO: 22) |
| YANQFM | (SEQ ID NO: 23) |
| ANQFMW | (SEQ ID NO: 24) |
| NQFMWE | (SEQ ID NO: 25) |
| QFMWEY | (SEQ ID NO: 26) |
| FMWEYS | (SEQ ID NO: 27) |
| EAFRK | (SEQ ID NO: 28) |
| AFRKD | (SEQ ID NO: 29) |
| DPKEY | (SEQ ID NO: 30) |
| ANQFM | (SEQ ID NO: 31) |
| WEYST | (SEQ ID NO: 32) |
| YANQF | (SEQ ID NO: 33) |
| ANQFM | (SEQ ID NO: 34) |
| NQFMW | (SEQ ID NO: 35) |
| QFMWE | (SEQ ID NO: 36) |
| FMWEY | (SEQ ID NO: 37) |
| MWEYS | (SEQ ID NO: 38) |

The practice of the present invention employs, unless otherwise indicated, conventional techniques of synthetic organic chemistry, protein chemistry, molecular biology, microbiology, and recombinant DNA technology, which are well within the skill of the art. These techniques are applied in connection with peptide synthesis, recombinant production of peptides and peptide mutagenesis, for example. Such techniques are explained fully in the literature. See e.g., Scopes, R. K., Protein Purification Principles and Practices, 2d ed. (Springer-Verlag. 1987), Methods in Enzymology (M. Deutscher, ed., Academic Press, Inc. 1990), Sambrook, et al., Molecular Cloning: A laboratory Manual, 2d ed., (Cold Spring Harbor Press, Cold Spring Harbor, N.Y., 1989), Handbook of Experimental Immunology, Vols. I-IV (D. M. Weir and C. C. Blackwell, eds., 1986, Blackwell Scientific Publications), House, Modern Synthetic Reactions, 2d ed., (Benjamin/Cummings, Menlo Park, Calif., 1972).

The peptides of the present invention, homologs, analogs and fragments thereof can be synthesized by a number of known techniques. For example, the peptides can be prepared using the solid-phase synthetic technique initially described by Merrifield, in J. Am. Chem. Soc. 85:2149-2154 (1963). Other peptide synthesis techniques can be found in M. Bodanszky, et al. Peptide Synthesis, John Wiley & Sons, 2d Ed., (1976) and other references readily available to those skilled in the art. A summary of polypeptide synthesis techniques can be found in J. Stuart and J. D. Young, Solid Phase Peptide Synthesis, Pierce Chemical Company, Rockford, Ill., (1984). Peptides may also be synthesized by solution methods as described in The Proteins, Vol. II. 3d Ed., Neurath, H. et al., Eds., p. 105-237, Academic Press, New York, N.Y. (1976). Appropriate protective groups for use in different peptide syntheses are described in the above-mentioned texts as well as in J. F. W. McOmie, Protective Groups in Organic Chemistry, Plenum Press, New York, N.Y. (1973). The peptides of the present invention can also be prepared by chemical or enzymatic cleavage from larger portions of the DBP molecule or from the entire DBP molecule.

Additionally, the peptides of the present invention can also be prepared by recombinant DNA techniques (see e.g. Current Protocols in Molecular Cloning Ausubel et al., 1995, John Wiley & Sons, New York); Sambrook et al., 1989, Molecular Cloning: A Laboratory Manual, Second Edition, Cold Spring Harbor Laboratory Press, New York; Coligan et al. Current Protocols in Immunology, John Wiley & Sons Inc., New York, N.Y. (1994)). The skilled artisan understands that any of a wide variety of expression systems can be used to provide the recombinant peptides of the present invention. The precise host cell used is not critical to the invention. The DBP antagonist peptides can be produced in a prokaryotic host (e.g. *E. coli*), or in a eukaryotic host (e.g., *S. cerevisiae* or mammalian cells, e.g. COS1, CHO, NIH3T3, and JEG3 cells, or in the cells of an arthropod, e.g. *S. frugiperda*). Such cells are available from e.g. the American Type Culture Collection, Manassas, Va. The method of transfection and the choice of expression vehicle will depend on the host system selected. Transformation and transfection methods are described, e.g. in Sambrook et al. supra; expression vehicles can be chosen from those provided e.g. in Cloning Vectors: A Laboratory Manual P. H. Powels et al (1985), Supp. 1987.

For most of the amino acids used to build proteins, more than one coding nucleotide triplet (codon) can code for a particular amino acid residue. This property of the genetic code is known as redundancy. Therefore, a number of different nucleotide sequences can code for a particular subject DBP antagonist peptide. The present invention also contemplates a deoxyribonucleic acid (DNA) molecule or segment that defines a gene coding for, i.e., capable of expressing, a subject peptide or a subject chimeric peptide from which a peptide of the present invention can be enzymatically or chemically cleaved.

DNA molecules that encode peptides of the present invention can be synthesized by chemical techniques, for example, the phosphotriester method of Matteuccie, et al., J. Am. Chem. Soc. 103:3185(1981). Using a chemical DNA synthesis technique, desired modifications in the peptide sequence can be made by making substitutions for bases which code for the native amino acid sequence. Ribonucleic acid equivalents of the above described DNA molecules may also be used.

A nucleic acid molecule comprising a vector capable of replication and expression of a DNA molecule defining coding sequence for a subject polypeptide or subject chimeric polypeptide is also contemplated.

The peptides of the present invention are chemically synthesized by conventional techniques such as the Merrifield solid phase technique. In general, the method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

A preferred method of solid phase synthesis entails attaching the protected or derivatized amino acid to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino carboxyl group is then removed from this newly added amino acid residue, and the next amino acid (suitably protected) is then added, and so forth. After all the desired amino acids have been linked in the proper sequence, any remaining terminal and side group protecting groups including the solid support are removed sequentially or concurrently to yield the final peptide. The lyophilized oligopeptides are resuspended in double distilled $H_2O$ at 2 mg/ml as stock solutions and subsequently diluted in M199-HPS for experiments.

Peptides SEQ ID NOs: 1 and 2 have the following sequences:

SEQ ID NO:1 EAFRKDPKEYANQFMWEYST

SEQ ID NO:2 E-A-F-$Xaa_1$-$Xaa_2$-D-P-$Xaa_3$-$Xaa_4$-$Xaa_5$-A-$Xaa_6$-$Xaa_7$-F-$Xaa_8$-$Xaa_9$-E-Y-S-$Xaa_{10}$ including homologs, analogs and fragments which maintain DBP antagonist activity; wherein A=Ala=Alanine
R=Arg=Arginine
N=Asn=Asparagine
D=Asp=Aspartate
B=Asx=Asparagine or Aspartate
C=Cys=Cysteine
Q=Gln=Glutamine
E=Glu=Glutamate
Z=Glx=Glutamine or Glutamate
G=Gly=Glycine
H=His=Histidine
I=Ile=Isoleucine
L=Leu=Leucine
K=Lys=Lysine
F=Phe=Phenylalanine
P=Pro=Proline
S=Ser=Serine
T=Thr=Threonine
W=Trp=Tryptophan
Y=Tyr=Tyrosine
V=Val=Valine
X=Xaa=Any amino acid Consistent with the observed properties of the peptides of the invention, the present peptides can be used to inhibit, suppress or cause the cessation of at least one DBP mediated activity. DBP functions in the biochemical events associated with the inflammation reaction in animals as an agonist to C5a /C5a des Arg in the induction of the migration of all kind of leukocytes. Accordingly, the present invention contemplates methods to block, interfere with or otherwise prevent the DBP enhancement of C5a/C5a des Arg chemotactic activity and thereby effectively treat C5a/C5a des Arg-mediated disorders.

In another embodiment of the present invention, one or more DBP antagonists, e.g., DBP antagonist peptides, are included in pharmaceutical compositions.

Compositions containing the DBP antagonist peptides of the present invention can be administered intramuscularly, subcutaneously, orally, nasally, topically or intravenously. Preferably, compositions containing the DBP antagonist peptides of the present invention are administered intravenously to inhibit, suppress, or cause the cessation of at least one DBP-mediated biological activity. When administered intravenously, the peptide compositions can be combined with other ingredients, such as carriers and/or adjuvants. The peptides can also be covalently attached to a protein carrier, such as albumin, so as to minimize clearing of the peptides. There are no limitations on the nature of the other ingredients, except that such ingredients must be pharmaceutically acceptable, efficacious for their intended administration and cannot degrade the activity of the active ingredients of the compositions. Examples of other anti-inflammatory ingredients contemplated by the present invention include, but are not limited to anti-CD4 antibodies, anti-TNF-alpha antibody, NSAIDS, steroids, IL-16 antagonists or cyclosporin-A. When employed together with DBP antagonists, these agents can be employed in lesser dosages than when used alone.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants or vegetable oils. Sterilization can be accomplished by any art-recognized technique, including but not limited to, filtration or addition of antibacterial or antifungal agents, for example, paraben, chlorobutano, phenol, sorbic acid or thimerosal. Further, isotonic agents such as sugars or sodium chloride may be incorporated in the subject compositions.

Production of sterile injectable solutions containing the subject peptides is accomplished by incorporated these compounds in the required amount in the appropriate solvent with various ingredients enumerated above, as required, followed by sterilization, preferably filter sterilization. To obtain a sterile powder, the above solutions are vacuum-dried or freeze-dried as necessary.

When the peptides of the invention are administered orally, the pharmaceutical compositions thereof containing an effective dose of the peptide can also contain an inert diluent, as assimilable edible carrier and the like, be in hard or soft shell gelatin capsules, be compressed into tablets, or may be in an elixir, suspension, syrup or the like.

The subject peptides are thus compounded for convenient and effective administration in pharmaceutically effective amounts with a suitable pharmaceutically acceptable carrier in a therapeutically effective dose.

The peptides can be administered in a manner compatible with a dosage formulation and in such amount as well be therapeutically effective. Systemic dosages depend on the age, weight and conditions of the patient and on the administration route.

As used herein, a pharmaceutically acceptable carrier includes any and all solvents, dispersion media, coatings, antibacterial and antifungal agents, isotonic agents the like. The use of such media and agents are well-known in the art. The pharmaceutically acceptable carriers used in conjunction with the peptides of the present invention vary according to the mode of administration. For example, the compositions may be formulated in any suitable carrier for oral liquid formulation such as suspensions, elixirs and solutions. Compositions for liquid oral dosage include any of the usual pharmaceutical media such as, for example, water, oils, alcohols, flavoring agents, preservatives, coloring agents and the like. In the case of oral solid preparations (capsules and tablets) carriers such as starches, sugars, diluents, granulating agents, lubricants, binders, disintegrating agents and the like may be used. In addition, carriers such as liposomes and microemulsions may be used.

In a further embodiment of the present invention, the pharmaceutical compositions of the present invention are employed for the treatment of C5a/C5a des Arg-mediated pathological disorders. Thus, the present invention provides methods of treating an C5a/C5a des Arg-mediated disorder in a subject by administering a therapeutically effective amount of a pharmaceutical composition of the present invention.

The term "therapeutically effective amount" means the dose required to treat a C5a/C5a des Arg-mediated disorder.

By "a C5a/C5a des Arg-mediated disorder" is meant a pathological disorder, the onset, progression or the persistence of the symptoms of which requires the participation of C5a or C5a des Arg molecules.

The term "treatment" or "treat" refers to effective inhibition, suppression or cessation of the DBP activity so as to prevent or delay the onset, retard the progression or ameliorate the symptoms of the C5a/C5a des Arg-mediated disorder.

The term "subject" refers to any mammalian subject. Preferably, the subject is a human.

The present invention thus provides methods of interfering with, blocking or otherwise preventing the action of DBP on C5a/C5a des Arg by employing the DBP peptide antagonists contemplated by the present invention.

In one embodiment, the present invention is directed to a method for treating C5a /C5a des Arg-mediated disorders, such as immunoinflammatory disorders, by administering to a subject in need of such treatment a therapeutic effective amount of the peptides or composition provided by the present invention.

The present invention recognizes a novel DBP binding/signaling complex comprising annexin A2, CD36, CD47 and CD44 that mediates the cochemotactic signal from DBP. Accordingly, in another embodiment, the present invention is directed to antagonist peptides or antibodies against CD36, CD47, CD44 and/or annexin A2 and a composition comprising such peptides or antibodies.

In still anther embodiment, the present invention is directed to a method for treating C5a /C5a des Arg-mediated disorders, such as immunoinflammatory disorders, by administering to a subject in need of such treatment a therapeutic effective amount of the antagonist peptides or antibodies against CD36, CD47, CD44 and/or annexin A2 provided by the present invention. For example, FIGS. 14A and 14B demonstrate that affinity-purified antibodies to CD36 and CD47 significantly inhibit U937-C5aR (FIG. 14A) and neutrophil (FIG. 14B) chemotaxis to zymosan-activated serum (ZAS), a DBP-dependent process, but not to purified C5a (DBP-independent migration). Antibodies to the receptor for the globular region of complement C1q (gC1qR, expressed on both cell types) was the negative control for the effect of antibodies binding to cell surface receptors.

Without intending to be limited to a particular theory, it is believed that the C5a chemotactic cofactor function of DBP is a specific example of a more generalized cellular response. It is believed that several soluble extracellular proteins (for example, complement C1q, fibrinogen, fibronectin, thrombospondin-1, DBP, vitronectin) can function as cell surface adapter molecules to bridge proteins that ordinarily would not interact with one another. In this way, they catalyze the assembly of novel signaling complexes, perhaps in lipid rafts, composed of several distinct proteins that serve as subunits of a nascent multifaceted receptor. It is believed that signaling can be initiated by the clustering action of the adapter molecule. Although these soluble proteins do not function as classic high affinity ligands per se, they do act as de facto ligands required for assembly and subsequent signaling of the complex. It is believed that different adapter molecules can initiate assembly of unique receptor complexes and, in this way, can "mix and match' cell surface molecules to achieve a desired signal and cellular response. These complexes probably function transiently and can be terminated rapidly by post-translational modifications such as proteolysis (cleavage and inactivation of a key protein and/or extracellular shedding of the complex), phosphorylation, dephosphorylation, deglycosylation, etc. Furthermore, it is believed that disease conditions can adversely affect the normal functioning of these complexes. Excessive or improper production of inflammatory mediators can trigger inadvertent generation or premature termination of physiological complexes, or conceivably, formation of aberrant pathological signaling complexes.

The DBP antagonist peptides of the present invention (or homologs, analogs or fragments) can be used to raise monoclonal antibodies useful in the invention. The peptides can be coupled to a carrier protein such as KLH as described in Ausubel et al. (1989) Current Protocols in Molecular Biology, John Wiley & Sons, New York. The KLH-antagonist peptide is mixed with Freund's adjuvant and injected into guinea pigs, rats, donkeys and the like or preferably into rabbits. Antibodies can be purified by peptide antigen affinity chromatography.

Monoclonal antibodies can be prepared using DBP antagonist peptides and standard hybridoma technology (see e.g. Kohler et al., (1975) Nature 256:495; Hammerling et al., (1981) In Monoclonal Antibodies and T Cell Hybridomas, Elsevier, N.Y.). For example, monoclonal antibodies to DBP antagonist peptides (homologs, analogs or fragments thereof) can be raised in Balb/C or other similar strains of mice by immunization with purified or partially purified preparations of DBP antagonist peptides. The spleens of the mice can be removed, and their lymphocytes fused to a mouse myeloma cell line. After screening of hybrids by known techniques, a stable hybrid will be isolated that produces antibodies against DBP antagonist peptides. Such activity can be demonstrated by the ability of the antibody to prevent the radiolabelled DBP antagonist peptide from interfering or blocking the DBP enhancement of C5a/C5a des Arg chemotactic activity. The monoclonal antibody can then be examined for its ability to inhibit the biological activity of DBP, e.g., the enhancement or augmentation of the C5a/C5a des Arg chemotactic activity. Once produced, monoclonal antibodies are tested for specific DBP recognition by Western blot or immunoprecipitation analysis (by methods described in Ausubel et al., supra). The antibodies of the present invention can be used in diagnostic assays or to further characterize DBP, DBP fragments or DBP antagonist peptides.

The invention is further illustrated by the following specific examples which are not intended in any way to limit the scope of the invention.

EXAMPLE 1

Materials and Methods

Reagents: Recombinant C5a was purchased from Sigma-Aldrich (St. Louis, Mo.). Purified human DBP was obtained from Biodesign International (Kennebunkport, Me.). Full-length human DBP cDNA (Gc-2 allele), clone number CS0DM004YF02, was purchased from Invitrogen (Carlsbad, Calif.). DNA restriction and modification enzymes were purchased from New England Biolabs (Beverley, Mass.). Oligonucleotides were synthesized by Invitrogen. Anti-human DBP was purchased from DiaSorin, (Stillwater, Minn.). pGEX4T-2 expression vector was purchased from Amersham BioSciences (Piscataway, N.J.). Dibutyryl-cAMP ($Bt_2$cAMP), DMSO, and protease inhibitor cocktail mixture was obtained from Sigma-Aldrich. Complement-activated serum using yeast cell walls (zymosan A) was prepared as previously described (Trujillo, G., and Kew, R. R. *J. Immunol.* 173, 4130-4136 (2004)). DBP-derived peptides, a peptide corresponding to residues 130-152 (EAFRKDPKEYANQFMWEYSTNYG (SEQ ID NO: 3), and a peptide with the sequence corresponding to residues 150-172 (NYGQAPLSLLVSYTKSYLSMVGS (SEQ ID NO: 4)), were synthesized and purified (>95% purity) by the American Peptide Company, Inc. (Sunnyvale, Calif.).

Cells and cell culture: Human promyelocytic cell line HL-60 was obtained from ATCC (Rockville, Md.) and cultured in RPMI 1640 medium supplemented with 10% FBS. Differentiation of HL-60 cells was initiated with 250 μM $Bt_2$cAMP for 48 hours.

Construction of full-length and truncated recombinant expressed DBP (reDBP). To construct GST fusion proteins, DNA sequences corresponding to the indicated regions of full-length human DBP or DBP domains were amplified by PCR, designed to generate products with 5' BamHI and 3' XhoI restriction site. The *E. coli* expressed proteins were designated as follows: full-length reDBP (residue 1-458), DBP domains I & II (residue 1-378), DBP domains II & III (residue 192-458), DBP domain I (residue 1-191), DBP domain II (residue 192-378), DBP domain III (residue 379-458) were cloned into the corresponding site using pGEX-4T-2 expression plasmid as GST fusion partners in *E. coli* (sequences of all primers available from the authors upon request). *E. coli* strain XL-1 Blue (Stratagene, Calif.) served as host for DNA manipulation and the *E. coli* strain BL-21 served the host for protein expression. Truncated versions of domain I (residues 1-175, 1-150, 1-125 and 1-112) also were expressed in *E. coli* as described above. Each construct was confirmed by DNA sequencing.

Expression and purification of full-length and truncated reDBP. DBP was expressed in *E. coli* according to the protocol described by Swamy et al. (see *Protein Express. Purif.* 10, 115-122 (1997)). BL21 cells carrying pGEX-4T-2 plasmids expressed fusion protein GST linked to the DBP constructs. *E. coli* were grown at room temperature (22-24° C.) in Luria Broth (LB) containing 100 μg/ml ampicillin and 50 μg/ml chloramphenicol until absorbance at 600 nm (Abs 600) was 0.4-0.6. The expression of fusion proteins was induced by the addition of 0.5-1.0 mM IPTG for 4-8 hours. Cells were collected by centrifugation at 5000× g. The *E. coli* pellets (from 1 liter) were resuspended in 40 ml TBS (50 mM Tris-HCl, pH 8.3, 150 mM NaCl) containing 0.2 mg/ml lysozyme, 0.1 % Triton X-100 and 2 ml of a protease inhibitor cocktail mixture. The cells were disrupted by sonication and insoluble material was removed by centrifugation at 12,000× g for 20 minutes. The detergent soluble cell lysate containing the expressed fusion protein was mixed with 1 ml of a 50% slurry of glutathione-agarose, preequilibrated in TBS. After several washes with TBS, the bound GST-DBP was eluted with 20 mM oxidized glutathione in 100 mM Tris Buffer, pH 8.3. The fusion protein was cleaved with thrombin and dialyzed against PBS to remove oxidized glutathione. GST was separated from recombinant DBP using glutathionesepharose 4B affinity column. Sequencing fidelities of the reDBPs were confirmed by N-terminal peptide sequencing.

Vitamin D3-binding assay. Competitive binding assays of natural DBP full-length and truncated reDBP with $^3$H-25-OH-D$_3$ were carried out according to a published procedure with minor modifications (see Swamy et al.). In a typical experiment, solutions containing natural DBP, reDBP (200 ng),$^3$H-25-OH-D$_3$ (0.1 pmol), 25-OH-D$_3$ (0.5-64 pmol) in 10 μl with 490 μl assay buffer (50 mM TrisHCl pH 8.3, 150 mM sodium chloride, 1.5 mM EDTA, 0.1% Triton X-100) were incubated at 4° C. for 20 hours followed by treatment with 100 μl 2.5% ice-cold Dextran-coated charcoal and centrifugation at 5000× g at 4° C. Clear supernatants from the centrifuged samples were mixed with scintillation cocktail and counted for radioactivity. Each sample was assayed in triplicate.

Ligand-induced calcium mobilization. Calcium mobilization studies were performed using the Fluo-3 AM probe as described previously (see Merritt, J. E. et al., *Biochem. J.* 269, 513-519 (1990)). Differentiated HL-60 cells (1×10$^7$ cells/ml) were resuspended in HBSS-1% BSA containing 2 μM Fluo-3 AM (Molecular Probes, Eugene, Oreg.) and incubated at 37° C. for 40 minutes. Cells incubated without the dye were used as a control to measure autofluorescence ($F_{min}$). Following the dye uptake, cells were washed twice then suspended at 5×10$^6$ cells/ml in HBSS containing 1% BSA. Half of the cell suspension was treated with 50 nM DBP for 30 min at room temperature, the other half served as the untreated control. For each measurement, 400 μl of cell suspension (with or without DBP) was added to a cuvette and stimulated with various concentrations of purified C5a at room temperature (22-24° C.). Fluorescence was then measured immediately using a Perkin-Elmer LS-5 fluorometer at 505 nm excitation, 526 nm emission for Fluo-3 AM. $F_{max}$ was measured by treating labeled cells with 60 μM digitonin. Intracellular free calcium concentrations were calculated using the following formula: $(Ca^{2+})=K_d(F-Fmin)/(Fmax-F)$, where $K_d=325$ nM for Fluo-3 according to manufacturer (Molecular Probes).

Chemotaxis assay. Chemotaxis was performed as described previously (see Kew, R. R. et al., *J. Leukoc. Biol.* 58, 55-58 (1995)). In brief, 35 μl of C5a (0.01 to 1 nM) in the chemotaxis buffer (HBSS with 1% BSA, 10 mM HEPES) were placed in duplicate in the lower chamber of a 48-well chamber (Neuroprobe, Md.). The lower compartments were covered with a 5 μm pore cellulose nitrate filter and then 50 μl of the cell suspension (2.5×10$^5$/well) was pipetted into the upper compartments. The chemotactic chamber was incubated for 1 hour at 37° C. in a humidified incubator with 5% CO$_2$. Following incubation, the filter was fixed, stained and mounted on a microscope slide. Cell movement was measured as the distance in microns that the leading front of the cells had migrated into the filter (see Zigmond, S. et al., *J. Exp. Med.* 137, 387 (1973)).

Data analysis and statistics. At least 3 experiments were performed for each assay. Results of several experiments were analyzed for significant differences among group means using analysis of variance (ANOVA) followed by Newman-Keul's multiple comparisons post-test utilizing the statistical software program InStat (GraphPad Software, San Diego, Calif.).

EXAMPLE 2

DBP enhancement of C5a-induced chemotaxis and Ca$^{2+}$ influx in differentiated HL-60 cells. Previous published work in our lab has demonstrated that neutrophils coincubated with DBP display significant increased movement to suboptimal concentrations (10 to 100 pM) of C5a, i.e., the cochemotactic effect. However, neutrophils are short-lived, terminally differentiated cells and cannot be genetically manipulated. A cell culture model for neutrophils is the promyelocytic cell line HL-60 that can be induced to differentiate into neutrophil-like cells using agents such as DMSO or Bt$_2$cAMP. Differentiation of HL-60 cells for 48 hours using 250 μM Bt$_2$cAMP induced expression of the C5a receptor and permitted both chemotaxis to C5a alone and significantly enhanced movement to C5a in the presence of purified natural DBP (FIG. 1A). These results were consistent with previous reports of the present inventor using neutrophils and indicate that differentiated HL-60 cells will serve as a good cell culture model to investigate the cochemotactic function of DBP.

Intracellular calcium mobilization is a rapid and well-characterized event in response to C5a binding to its receptor. FIG. 1B shows that cells pretreated with DBP for 30 min displayed a significantly enhanced intracellular calcium influx in response to C5a. In contrast, untreated cells that had DBP and C5a added simultaneously did not show augmented calcium influx supporting previous studies showing that DBP needs to bind to the cell surface for at least 15 minutes before enhanced chemotaxis is observed (see Kew, R. R. et al., *Immunol.*155, 5369-5374 (1995)). This finding suggest the formation of a DBP signaling complex on the plasma membrane (see Trujillo, G. et al., *J. Immunol.* 173, 4130-4136 (2004)). The results presented in FIG. 1 show that DBP can enhance C5a-induced chemotaxis and calcium mobilization in differentiated HL-60 cells and indicate that this cell line will serve as a good cell culture model to investigate the cochemotactic function of DBP. The demonstration of DBP-mediated increase in calcium flux to C5a is particularly important because it will permit dissection of intracellular signaling pathways triggered by DBP bound to the cell surface.

EXAMPLE 3

Figure 2:
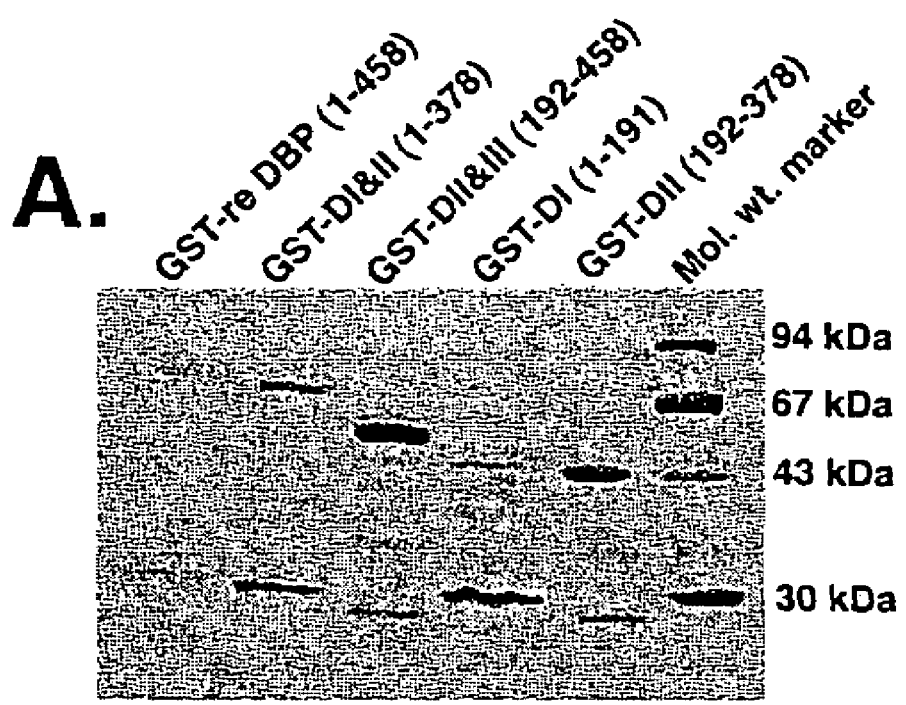
Figure 2:
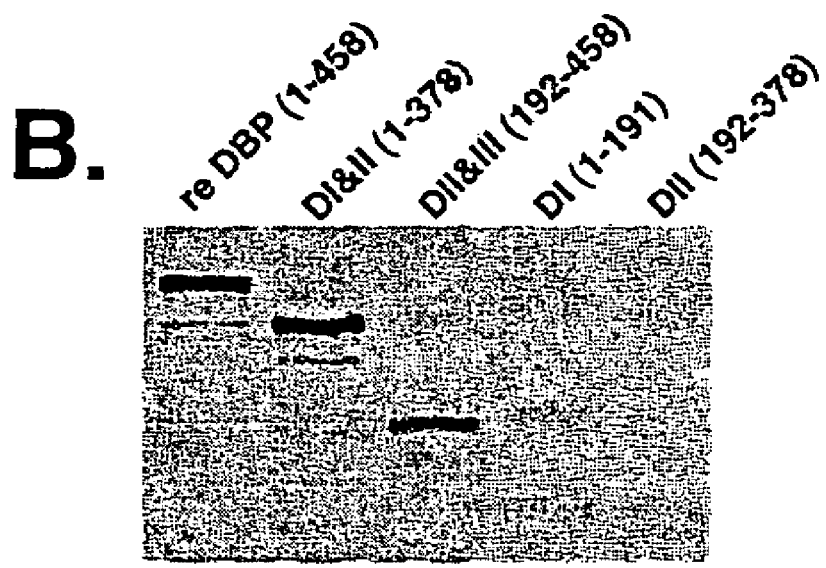
Figure 3:
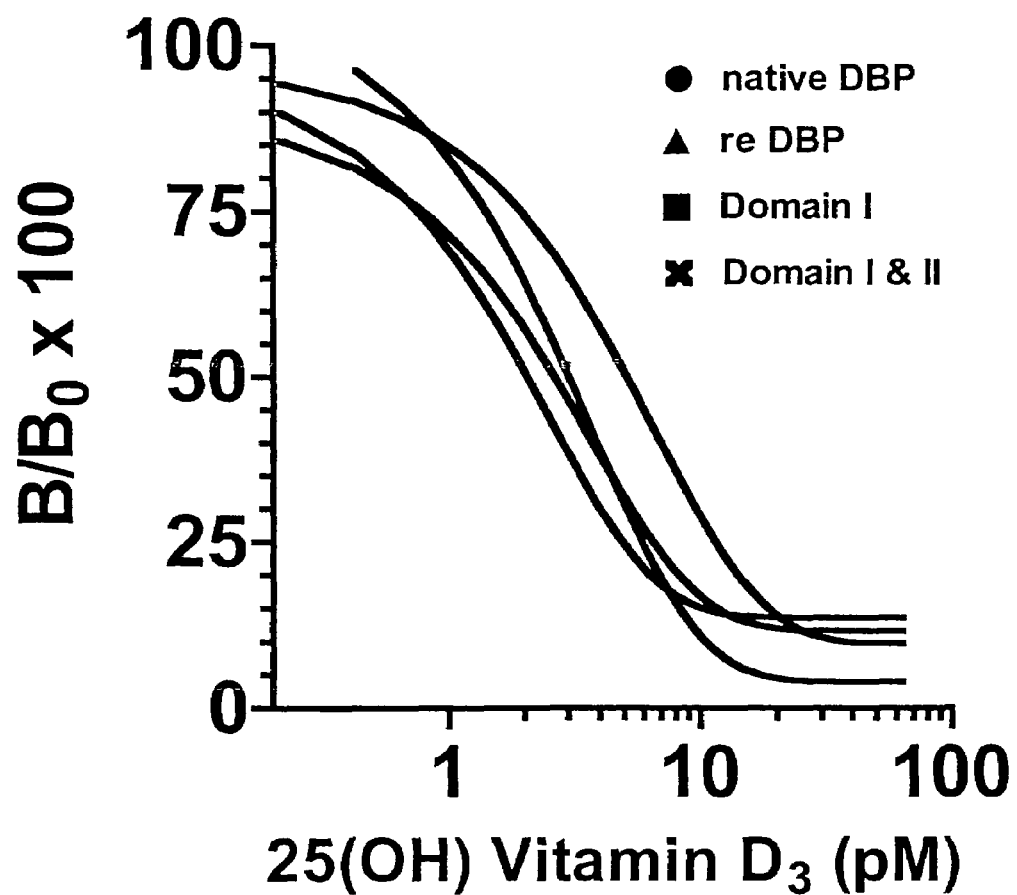

Analysis of *E. coli* expressed DBP by SDS-PAGE and western blotting. The commercially available (Invitrogen) 1374-nucleotide DBP cDNA, Gc2 allele, was expressed in *E. Coli* BL-21 in the plasmid vector pGEX-4T-2 fused to GST. Upon IPTG induction, the GST-DBP fusion protein was expressed, as judged by SDS-PAGE (FIG. 2A). SDS-PAGE of the elution protein revealed an ~80 kDa band corresponding to the molecular weight of full-length DBP fused to GST. The bands at ~65 kDa, 55 kDa, 45 kDa correspond to the molecular weight of GST with truncated forms of DBP. All lanes have a small amount of a 30 kDa band. This probably represents degradation product of GST or the unfinished product of the protein synthesis. Thrombin-cleavage of the purified fusion protein resulted in separation of GST from DBP. The SDS-PAGE and immunoblotting after cleavage and separation of GST revealed a single protein band of 56 kDa for full-length DBP, 40 kDa for domains I & II, 30 kDa for domains II & III, and 20 kDa for domain I or domain II (FIG. 2B).

EXAMPLE 4

Functional characterization of reDBP. The capacity of reDBP to bind 25(OH)-vitamin D$_3$ was measured to determine if the expressed proteins could functionally bind a physiological ligand. Competitive binding assays of reDBP with a fixed amount of $^3$H-25(OH)-D$_3$ and various amounts of unlabeled 25(OH)-D$_3$ demonstrate that all reDBP could displace the radiolabel in a similar dose-dependent manner (FIG.

Figure 4:
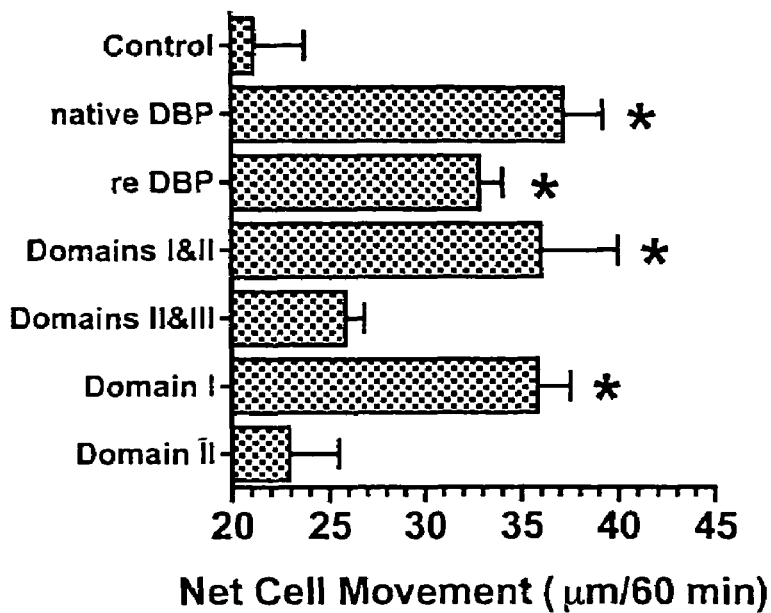
Figure 4:
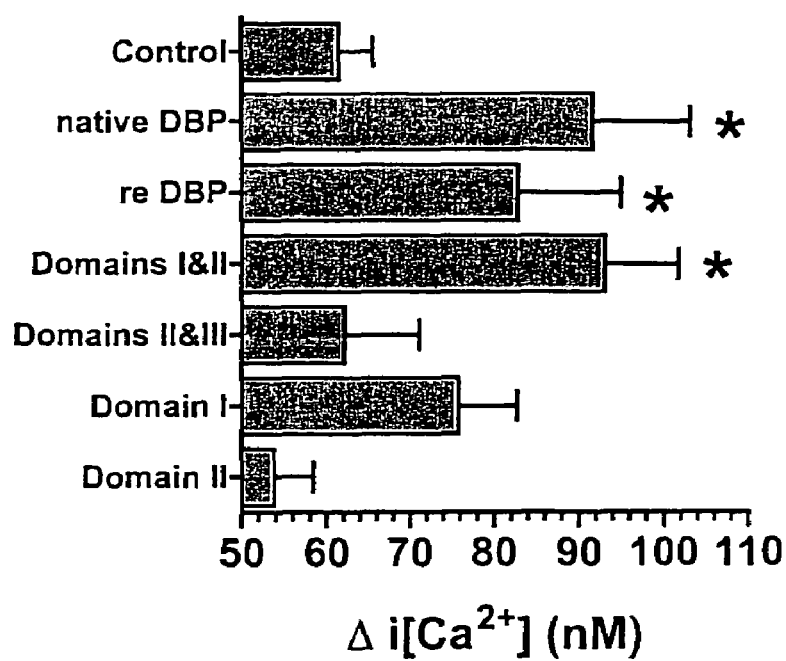

3), indicating that the vitamin D sterol binding site of the reDBPs is similar to the purified, natural DBP. In addition, full-length reDBP bound G-actin in a 1:1 molar complex as detected by non-denaturing PAGE (data not shown). The ability of reDBPs to enhance C5a-mediated chemotaxis and $Ca^{2+}$ flux in differentiated HL-60 cells was determined next. FIG. 4 demonstrates that reDBPs containing the N-terminal Domain I have the capacity to enhance chemotaxis (FIG. 4A) and intracellular $Ca^{2+}$ flux (FIG. 4B) in response to a C5a stimulus. Cells treated with DBP alone showed no response. In addition, undifferentiated HL-60 cells, that express very little C5a receptor, did not react to C5a or C5a plus DBP.

Figure 5:
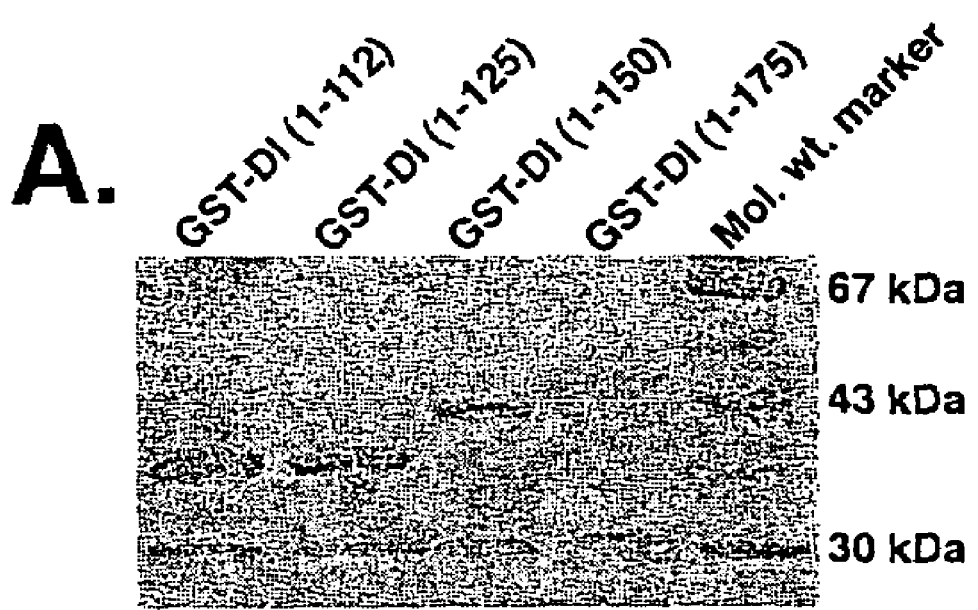
Figure 5:
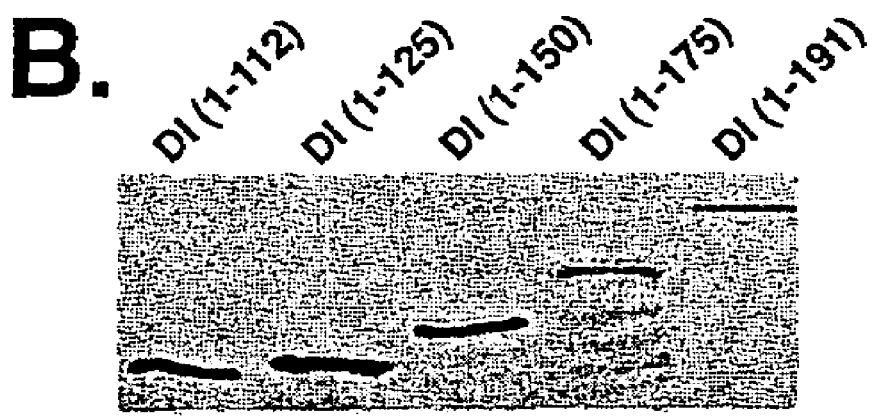
Figure 6:
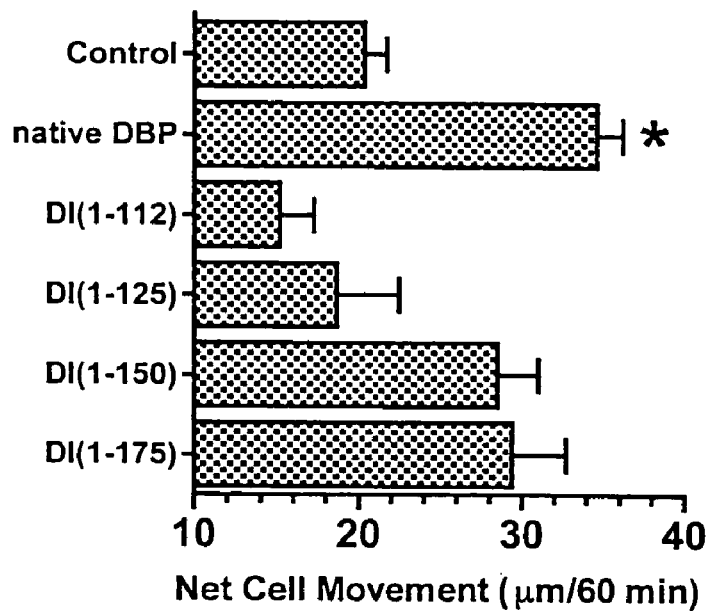
Figure 6:
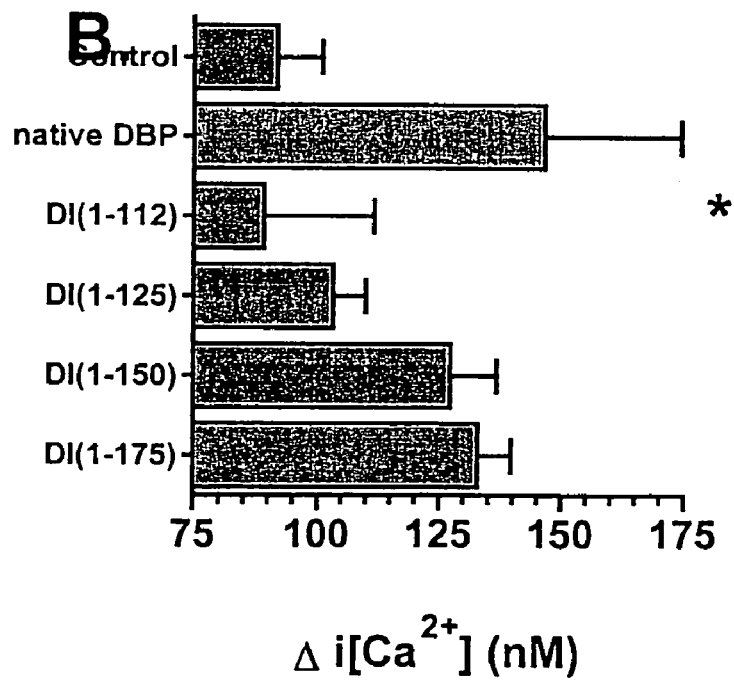

Previous results clearly demonstrate that the C5a cochemotactic function of DBP resides in the N-terminal domain. Therefore, in order to identify the cochemotactic sequence within this region, a series of truncated versions of domain I were generated. Initially, constructs containing either the N-terminal (amino acids 1-112) or C-terminal half (amino acids 113-191) of domain I were produced. The recombinant protein representing the N-terminal half of domain I (1-112) was expressed and purified but possessed no chemotactic enhancing activity for C5a (FIGS. 5 and 6). Several attempts to express the C-terminal half of domain I (113-191) in E. coli, however, failed repeatedly. The alternative approach of generating C-terminal truncations of domain I was employed next. Full-length domain I (1-191) was progressively truncated to (1-112) since this protein had no chemotactic enhancing activity. FIG. 5 shows the analysis of domain I truncations by SDS-PAGE (FIG. 5A) and immunoblotting (FIG. 5B). FIG. 6 demonstrates that domain I truncations (1-112) and (1-125) lack enhancing activity whereas (1-150) and (1-175) possess almost the same level of activity as full-length natural DBP for both chemotaxis (FIG. 6A) and $Ca^{2+}$ flux (FIG. 6B).

Figure 7:
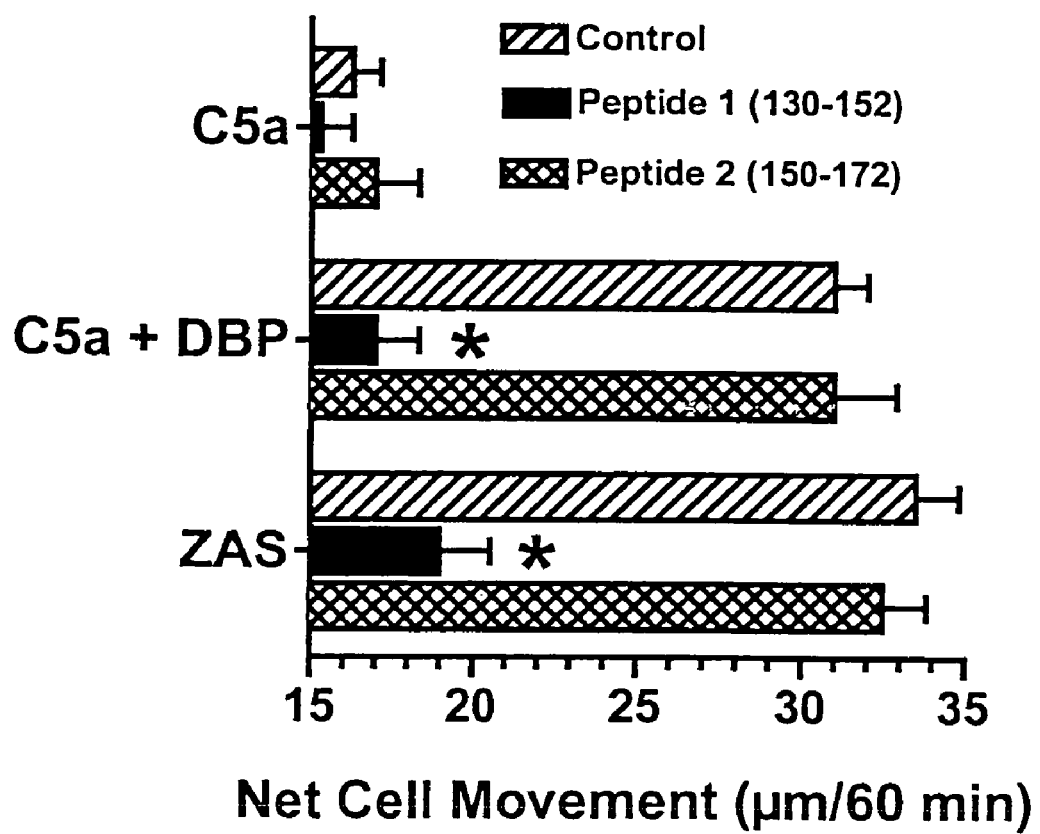

The results from FIG. 6 indicate that a region within domain I of DBP, from amino acids 126 to 175, is critical for the C5a cochemotactic function. Two overlapping peptides within this region of DBP next were synthesized to determine more precisely the sequence that is critical for cochemotactic activity of DBP. The peptide of SEQ ID NO: 3 (residues 130-152, EAFRKDPKEYANQFMWEYSTNYG) and the peptide of SEQ ID NO: 4 (residues 150-172, NYGQAPLSLLVSYTKSYLSMVGS) by themselves or mixed together could not enhance C5a-mediated chemotaxis. Consequently, an alternative approach of using these peptides to block the cochemotactic function of full-length natural DBP by pretreating cells with each peptide was employed. The results from FIG. 7 clearly show that the peptide of SEQ ID NO: 3 (130-152), but not the peptide of SEQ ID NO: 4 (150-172), could completely block the cochemotactic function of purified full-length natural DBP (C5a+DBP). In addition, the peptide of SEQ ID NO: 3 (130-152) also could eliminate the HL-60 cell chemotactic response to complement-activated serum (ZAS), indicating that this peptide can function to block a potent chemotactic signal in a diverse protein mixture (FIG. 7).

Further analysis of these results demonstrate that the cochemotatic function of DBP is confined to the amino acid sequence corresponding to amino acid residues 130-149. The sequence corresponding to amino acid residues EAFRKDPKEYANQFMWEYST (130-149) is identical among the three major allelic forms of human DBP (Gc-1F, Gc-1S, Gc-2). In fact, there was no difference in the C5a chemotic function among these DBP isoforms (see Binder, R. et al.).

BLAST search of the sequence corresponding to amino acid residues 130-149 of human DBP produced no other match in any eukaryote, besides DBP, indicating that this region is unique to DBP. As Table 1 indicates, BLAST alignment of this sequence shows substantial correspondence among sequences in rat, mouse, rabbit and chicken. Table 1 also shows substantial similarity in the alignment with the corresponding sequence for turtle (see Paul Licht and Leigh Hunt, Identification and Structural Characterization of a Novel Member of the Vitamin D Binding Protein family, <http://ist-socrates.berkeley.edu/~licht/DBPcDNA_abstract.htm>).

Several recent reports have described the crystal structure of DBP, either unligated or bound to G-actin or vitamin D (see Verboven, C. et al.; Swamy, N. et al.; Head, J. F. et al.; Otterbein, L. R. et al.). Analysis of the structure has revealed that the protein is comprised of a series of alpha-helices, much like albumin (see He, X. M., and Carter, D. C. Nature 358, 209-215 (1992)), but in contrast to albumin, DBP folds into a hook-like structure that serves as the G-actin binding site (see Mizwicki, M. T., and Norman, A. W. J. Bone Miner. Res. 18, 795-806 (2003)). The cochemotactic sequence in DBP (residues 130-149) is located partly in alpha-helix number 7 (residues 125-134) but mostly in alpha-helix number 8 (residues 136-150) in domain I (see Verboven, C. et al.; Swamy, N. et al.; Head, J. F. et al.; Otterbein, L. R. et al.). Three-dimensional analysis of DBP crystal structure using the NIHNCBI software program Cn3D (version 4.1) indicated that this region is not blocked when DBP binds G-actin or vitamin D sterols and is accessible to interact with cells. This structural analysis correlates well with recent functional studies of the present inventor that demonstrated that ligation of DBP with either G-actin, 25-OH vitamin $D_3$ or both did not alter the C5a cochemotactic activity of DBP (Shah et. al., manuscript submitted). Therefore, this cochemotactic peptide is a distinct functional sequence.

EXAMPLE 5

Selective inhibition of the C5a chemotactic cofactor function of the Vitamin D binding protein by $1,25(OH)_2$ Vitamin D3

Materials and Methods

Reagents Purified human Vitamin D binding protein was purchased from Biodesign international (Kennebunkport, Me.). Purified recombinant human C5a, formyl norleucyl-leucyl-phenylalanine (fNLP), leukotriene B4 (LTB4) and zymosan A (yeast cell walls from S. cerevisiae) were purchased from Sigma-Aldrich (St. Louis, Mo.). Complement-activated serum was generated by incubating 1 ml of human serum with 10 mg zymosan A for 1 h at 37° C. Particulate matter was removed by centrifugation (1 5,000× g) and samples were aliquoted and frozen at −80° C. Recombinant CXCL8 (IL-8)was obtained from R&D Systems (Minneapolis, Minn.). The 25(OH) and $1,25(OH)_2$ forms of Vitamin D3 were purchased from BioMol (Plymouth Meeting, Pa.). G-actin was purified from rabbit skeletal muscle as previously described (Spudich and Watt, 1971).

Isolation of human neutrophils Neutrophils, serum, and plasma were isolated from the venous blood of healthy, medication-free, paid volunteers who gave informed consent. The Institutional Review Board of Stony Brook University approved this procedure. These procedures have been described in detail previously (Kew et al., 1995a).

Quantitative binding of radioiodinated DBP to neutrophils Purified DBP (200-400 µg) was iodinated using Na-$^{125}$I (Dupont-NEN, Wilmington, Del.) as previously described (DiMartino and Kew, 1999). Neutrophils (107 cells/sample) were incubated with 100 nM $^{125}$I-DBP in Hank's balanced salt solution (HBSS) containing 0.1% bovine serum albumin (BSA) (assay buffer) in a total volume of 100 μl. Samples were incubated at 37° C. for 60 min after which cells were placed on ice and then washed twice with ice-cold assay buffer (1.0 ml each) and centrifuged for 7 min at 200× g at 2° C. The cell pellets were then counted for total radioactivity in a gamma counter. All samples were assayed in triplicate or quadruplicate.

Neutrophil chemotaxis assay Cell movement was quantitated using a 48 well microchemotaxis chamber (Neuroprobe, Cabin John, Md.) and 5.0 μm pore size cellulose nitrate filters (purchased from Neuroprobe) as previously described (Kew et al., 1995a). Cell suspensions and chemotactic factors were prepared and/or diluted in the chemotaxis assay buffer (Hank's balanced salt solution supplemented with 10 mM HEPES (pH 7.4) and 1% bovine serum albumin). Cell movement was quantitated microscopically by measuring the distance in microns (μm) that the leading front of cells had migrated into the filter according to the method described by Zigmond and Hirsch (1973). In each experiment, five fields per duplicate filter were measured at 400× magnification. The value of the background controls (untreated cells responding to buffer) has been subtracted in all cases so that the data are presented as net neutrophil (PMN) movement in_m/time of incubation. The mean migration distance of the untreated buffer control from all experiments was 45±3.4 Sun/30 min (n=24).

Neutrophil alkaline phosphatase assay Alkaline phosphatase activity on the plasma membrane of viable neutrophils was measured using the fluorescent substrate 6,8-difluoro-4-methylumbelliferyl phosphate (DiFMUP) and the EnzChek Phosphatase Assay Kit (Molecular Probes, Eugene, Oreg.). Neutrophils ($5 \times 10^6$ cells) were suspended in 50 μl of 0.1M sodium acetate (pH 5.0) and were immediately added to microtiter plates containing 50 μl of 0.2mM DiFMUP substrate and incubated for 5 min at 22° C. in the dark. A standard curve was generated using known amounts of the fluorescent compound 6,8-difluoro-7-hydroxy-4-methylcoumarin. Fluorescence was measured at 358 nm excitation and 455 nm emission using a SpectraMax M2 microtiter plate reader (Molecular Devices, Sunnydale, Calif.).

Data analysis and statistics A minimum of three experiments was performed for each assay using neutrophils from different individuals. Results from several experiments were analyzed for significant differences among group means using the Newman-Keul's multiple comparisons test utilizing a statistical software program InStat (GraphPad Software, San Diego, Calif.).

Previous work from the present inventors' group has demonstrated that the binding of DBP to neutrophils is essential for the chemotaxis enhancement of C5a (Kew et al., 1995a, 1995b). More recent studies have shown that the region of DBP that mediates co-chemotactic activity resides in its N-terminal domain, distinct from the Vitamin D sterol or G-actin binding regions (Zhang and Kew, 2004). Therefore, to determine if ligation of DBP with eitherVitaminDand/or G-actin alters the ability to bind to neutrophils, the binding of apo (unligated) versus holo forms of radioiodinated DBP to neutrophils was measured. The binding of G-actin to $^{125}$I-DBP was confirmed by complex formation on gel filtration chromatography; the binding of Vitamin D was confirmed by measuring the inhibition of $^3$H-Vitamin D binding to DBP in the presence of unlabeled competitor vitamin. The result shows that saturation of DBP with Vitamin D, G-actin or both ligands does not alter its ability to bind to neutrophils, suggesting that the cellular binding region on DBP is distinct from either the Vitamin D sterol or G-actin binding sites. Since cell binding is prerequisite for C5a co-chemotaxis, the co-chemotactic activity of apo versus holo forms of DBP was measured. The result demonstrates that G-actin and the major plasma form of Vitamin D (25(OH)D3), bound to DBP either individually or together, did not alter its ability to enhance neutrophil chemotaxis toward C5a. However, the hormonally active form of Vitamin D (1,25(OH)$_2$D3) bound to DBP completely eliminated the co-chemotactic effect, despite the fact that this form of the vitamin did not alter DBP binding to neutrophils. The concentration of 1,25(OH)$_2$D3 used in the experiment (100 nM) is about 1000-fold greater than the physiological plasma concentration of the active vitamin. Therefore, to determine the effect of various concentrations of Vitamin D on the co-chemotactic activity of DBP, dose-response curves were generated.

The result also shows that 25(OH)D3 bound to DBP had no effect on co-chemotactic activity over a wide concentration range (10.6 to 10.13 M). In contrast, 1,25(OH)$_2$D3 bound to DBP completely inhibited its C5a co-chemotactic activity from 1 μM (10.6 M) to 10 pM(10. 11 M), and there was significant inhibition at 1 pM. These inhibitory levels of 1,25 (OH)$_2$D3 are well within the physiological concentration range (40-100 pM). These results indicate that only the active form of Vitamin D (1,25(OH)$_2$D3) inhibits the co-chemotactic effect of DBP.

The previous experiments demonstrated that 1,25(OH)$_2$D3 bound to DBP was a potent inhibitor of C5a co-chemotaxis. Therefore, the next question we addressed was does 1,25 (OH)$_2$D3 need to be bound to DBP to have an inhibitory effect. For these experiments, we exploited the fact that 25(OH)D3 binds to DBP with a 10-fold tighter affinity than does 1,25(OH)$_2$D3 (Cooke and Haddad, 1989), and that the 25(OH)D3 form of the vitamin does not alter the co-chemotactic activity of DBP. The present Example shows that, at a physiological concentration of 100 pM, 1,25(OH)$_2$D3 needs to be bound to DBP to inhibit co-chemotaxis. However, very high concentrations of free 1,25(OH)$_2$D3 (>10 nM) could inhibit the co-chemotactic function of DBP. Next, the effect of 1,25(OH)$_2$D3 on neutrophil movement toward other chemotactic stimulus was examined. The result demonstrates that 10 nM 1,25(OH)$_2$D3 bound to DBP does not alter neutrophil chemotaxis to optimal concentrations of C5a, formyl peptide, LTB4 or CXCL8 (IL-8), indicating that even super physiological concentrations of the active vitamin do not alter the chemotactic capacity of neutrophils. These results indicate that 1,25(OH)$_2$D3 selectively inhibits the co-chemotactic activity of DBP. Finally, the possible mechanism of the selective inhibition of DBP co-chemotactic activity by 1,25 (OH)$_2$D3 was investigated. Neutrophils express abundant quantities of the enzyme alkaline phosphatase on their plasma membranes (Borregaard et al., 1995) and 1,25(OH)$_2$D3 has been shown to increase the activity of this enzyme in several non-myeloid cell types (Gill and Bell, 2000; Mulkins et al., 1983; Schwartz et al., 1991). Furthermore, a plasma membrane form of the Vitamin D receptor (VDR) that mediates rapid signaling events has been described recently and this receptor associates with annexin A2 in lipid rafts (Huhtakangas et al., 2004; Mizwicki et al., 2004). AP on the external face of the plasma membrane also has been shown to associate with annexin A2 in lipid rafts (Gillette and Nielsen-Preiss, 2004). Moreover, our lab has recently shown that annexin A2 may serve as a part of the DBP cell surface binding site (McVoy and Kew). These studies have provided the rationale to investigate if there is an association between 1,25(OH)$_2$D3 and AP. Therefore, the effect of 1,25(OH)$_2$D3 and the phosphatase inhibitor sodium orthovanadate (SOV) on neutrophil AP activity and co-chemotactic activity was examined. AP activity was measured on viable purified neutrophils ($5 \times 10^6$ cells) using the fluorescent substrate DiFMUP. As expected neutrophils contained abundant AP activity (11,107±1335 units); however, enzyme activity was not significantly altered by pretreating cells with 10 nM 1,25(OH)$_2$D3. In contrast, 10 µM SOV almost completely inhibited neutrophil AP activity (667±111 units) but did not alter cell viability. FIG. 5 demonstrates that pretreating neutrophils with 10 µM SOV also completely reverses the inhibitory effect of 1,25(OH)$_2$D3 on the C5a co-chemotactic activity of DBP, while SOV alone has no effect on the cells ability to migrate towards C5a plus DBP. This data suggests that 1,25(OH)$_2$D3 requires AP activity to inhibit the cochemotactic function of DBP.

EXAMPLE 6

CD44 and Annexin A2 Mediate the C5a Chemotactic Cofactor Function of the Vitamin D Binding Protein Materials and Methods Reagents Purified recombinant human C5a was purchased from Sigma-Aldrich. DBP was purified from human plasma and purchased from Biodesign International. BSA, goat IgG, ionomycin, DNase I, chondroitinase AC, and zymosan A (yeast cell walls from Saccharomyces cerevisiae) were obtained from Sigma-Aldrich. The protease inhibitors PMSF and 1,10-phenanthroline were purchased from Sigma-Aldrich, whereas Pefabloc SC and E-64 were purchased from Roche Applied Science. Polyclonal Abs to CD44 and annexin A2, directed against a specific peptide epitope, were produced in goats. The affinity-purified Abs, CD44 (N-18) and annexin A2 (C-16) and their corresponding peptide Ags (Ag blocking peptide) were obtained from Santa Cruz Biotechnology. Polyclonal anti-DBP was purchased from Dia-Sorin and then affinity-purified using immobilized DBP. Monoclonal anti-DBP (MAK-89) was a generous gift from the late Dr. J. Haddad (University of Pennsylvania, Philadelphia, Pa.). Sterile, pyrogen-free water, HBSS, PBS, RPMI 1640, and 1 M HEPES solution were purchased from Mediatech.

Isolation of Human Blood Products

Neutrophils, serum, and plasma were isolated from the venous blood of healthy, medication-free, paid volunteers who gave informed consent. The Institutional Review Board of Stony Brook University approved this procedure. These procedures have been described in detail previously (15).

In vitro Culture of U937 Cells

U937 cells were originally obtained from the American Type Culture Collection and transfected with either the human C5a receptor or the empty plasmid vector as detailed previously (16). U937 cells were cultured at 37° C., 5% CO2 in RPMI 1640 containing 10% FBS (HyClone) and 400_g/ml active G418 (Invitrogen Life Technologies) and maintained at a density between $2 \times 10^5$ and $1.5 \times 10^6$/ml.

Preparation of C-Activated Serum and Plasma

Serum and citrated plasma (1 ml each) were incubated for 1 h at 37° C. with 10 mg of zymosan. Particulate matter was removed by centrifugation (15,000× g) for 5 min at 4° C. using a microfuge. Samples were then aliquoted and frozen at −20° C.

Chemotaxis Assay

Cell movement was quantitated using a 48-well microchemotaxis chamber (NeuroProbe) and 5.0-µm pore size cellulose nitrate filters (purchased from NeuroProbe) as previously described (13). Cell movement was quantitated microscopically by measuring the distance in micrometers that the leading front of cells had migrated into the filter according to the method described by Zigmond and Hirsch (17). In each experiment, five fields per duplicate filter were measured at ×400 magnification. The value of the background controls for random cell movement (cells responding to buffer) has been subtracted in all cases so that the data are presented as net movement in micrometers.

DBP Binding Assay

DBP was labeled with AlexaFluor 488 Protein Labeling kit (Molecular Probes) according to the manufacturer's instructions. U937-C5aR cells ($50 \times 10^6$ cells/ml) in HBSS were pretreated with 100 nM ionomycin for 15 min at 37° C. The cells were then treated with protease inhibitor mixture (2 mM PMSF, 2 mM 1,10-phenanthroline, 0.5 mM E-64, and 0.5 mM Pefabloc), to prevent shedding of the DBP binding site, and incubated with 1 µM AlexaFluor 488-labeled DBP in HBSS containing 0.1% BSA (assay buffer) at 37° C. for 45 min. After the incubation period, cells were washed in HBSS and resuspended in assay buffer and the relative fluorescence was measured using a Spectramax M2 (Molecular Devices). All samples were assayed in triplicate.

Coimmunoprecipitation, SDS-PAGE, and Autoradiography

Purified DBP (200 µg) was radiolabeled using Iodobeads (Pierce) and Na$^{125}$I as previously described in detail (10). Neutrophils ($100 \times 10^6$ cells) in 2 ml of HBSS were incubated with 0.4 µM $^{125}$I-labeled DBP at 37° C. for 60 min and then washed twice in HBSS. Cells were resuspended in lysis buffer (1% Triton X-100, 50 mM HEPES, 0.01% SDS) containing a protease inhibitor mixture (see DPB binding assay) and 1 mg/ml DNase I. After incubation at 37° C. for 1 h, lysates were precleared with an irrelevant goat IgG for 1 h at 37° C., followed by 25 µl of protein G-Sepharose also for 1 h at 37° C. The lysates were then incubated with affinity-purified polyclonal goat anti-DBP or goat anti-CD44 for 1 h at 37° C. The immune complexes were isolated with 25 µl of protein G-Sepharose for 1 h at 37° C. Sepharose beads were washed twice in lysis buffer, and immunoreactive proteins were eluted from the protein G with SDS-PAGE sample buffer at 100° C. for 10 min. Immunoprecipitates were separated by SDS-PAGE using an 8-16% gradient polyacrylamide gel (BioRad). The gel was fixed in 40% methanol and 10% acetic acid, rehydrated in dH$_2$O with 5% glycerol, dried, and exposed to x-ray-film at −80° C.

Confocal Microscopy

U937-Ca5R cells or neutrophils were suspended in HBSS plus 0.1% BSA at $5 \times 10^6$/ml. Cells were stimulated with 100 nM ionomycin for 15 min at 37° C. followed by treatment with the protease inhibitor mixture (to prevent shedding of the DBP binding site). Purified DBP (1 µM) was then added to the cells for 30 min at 37° C. and then washed. Cells were incubated with mouse monoclonal anti-DBP (MAK-89), an irrelevant goat IgG, goat anti-CD44, or goat anti-annexin A2 for 30 min on ice. After washing, cells were incubated first with AlexaFluor 647-labeled donkey anti-goat IgG for 30 min on ice in the dark. Finally, after washing, AlexaFluor 488-labeled goat anti-mouse IgG was added for 30 min on ice in the dark. Cells were then washed twice in HBSS and fixed in 2% paraformaldehyde for 20 min then analyzed by confocal microscopy at ×400 magnification. Cell pellets were resuspended in 20 µl of mounting medium/antifade reagent (Molecular Probes), mounted on glass slides with no. $1^{1/2}$ coverslips, and allowed to dry overnight. All samples were visualized using a Leica TCS SP2 confocal microscope, and images were processed using Adobe Photoshop.

Data Analysis and Statistics

A minimum of three experiments was performed for each assay. Results of several experiments were analyzed for significant differences among group means using ANOVA followed by Newman-Keul's multiple comparisons posttest using the statistical software program InStat (GraphPad).

Results

Cell surface molecules that may mediate the C5a chemotactic cofactor function of DBP were investigated using both U937-C5aR cells and neutrophils. In addition, both C-activated serum and C-activated plasma were used as chemoattractants (a source of C5adesArg plus DBP) because U937-C5aR cells show significantly increased chemotaxis to Cactivated serum as compared with C-activated plasma (15). This differential response, most prominently observed in U937-C5aR cells, is due to the presence of platelet-derived thrombospondin-1 in serum that facilitates the cochemotactic activity of DBP (15). Previous work from this lab using purified neutrophil plasma membrane preparations has demonstrated that DBP binds to a CSPG (10). To verify that a CSPG mediates the C5a chemotactic cofactor effect of DBP in U937-C5aR cells, chondroitin sulfate side chains were removed using either the enzyme chrondroitinase AC or cells were grown in 20 mM sodium chlorate, which inhibits sulfation of the glycosaminoglycan side chain.

The result demonstrates that either treatment significantly reduces U937-C5aR chemotaxis to an optimal concentration (2.5%) of C-activated serum but not to 2.5% C-activated plasma, indicating that a CSPG is required for DBP to function as a chemotactic cofactor. In addition, chemotaxis to 1 nM purified C5a (an optimal concentration), a DBP-independent process, was not altered by either chondroitinase (control, 57+/−4.0; chondroitinase, 58+/−2.6 μm/120 min) or chlorate (control, 62+/−4.7; chlorate, 56+/−4.8 μm/120 min) treatment of cells, indicating that treated cells possessed the capacity for a vigorous chemotactic response to C5a. There are several different CSPGs on the surface of neutrophils and U937 cells, but CD44 is a particularly appealing candidate to be associated with the cochemotactic function of DBP. CD44 is a widely expressed type I transmembrane glycoprotein that has promiscuous binding properties and plays a role in migration of many cell types including leukocytes (18). To examine the function of CD44 in this process, cells were pretreated with an affinity-purified polyclonal anti-CD44 or an irrelevant goat IgG and then allowed to migrate toward either C-activated serum or C-activated plasma. The result shows that anti-CD44 significantly reduces both U937-C5aR cell and neutrophil movement toward C-activated serum, but not C-activated plasma. Moreover, anti-CD44 treatment did not alter chemotaxis to 1 nM purified C5a for either U937-C5aR cells (control, 51+/−3.9; anti-CD44, 46+/−2.7 μm/120 min) or neutrophils (control, 44+/−3.9; anti-CD44, 44+/−5.3 μm/25 min), further indicating that the inhibitory effect is specific for the cochemotactic function of DBP. In addition, pretreatment of anti-CD44 with its corresponding antigenic peptide (i.e., Ag blocking peptide) completely reversed the effect of anti-CD44 on chemotaxis to C-activated serum, confirming that the Ab mediates the inhibitory effect by binding to a CD44 peptide epitope. To determine whether DBP physically associates with CD44, coimmunoprecipitation studies were performed. For this experiment, $^{125}$Ilabeled DBP was incubated with neutrophils to allow the protein to bind surface ligands. After detergent solubilization and a preclearing step with goat IgG, cell lysates were immunoprecipitated with anti-CD44, anti-DBP (positive control), or goat IgG (negative control, data not shown). The present Example demonstrates that radiolabeled DBP immunoprecipitates with anti-CD44 in neutrophils indicating a physical association between the two molecules. Furthermore, analysis of CD44 and cell-associated DBP by confocal microscopy shows a large overlap in the merged signal on the cell surface.

These results clearly demonstrate that DBP associates with cell surface CD44 and this glycoprotein plays a role in mediating the cochemotactic activity of DBP. CD44 has been shown to associate with several cell surface macromolecules, some of which may participate in the formation of a DBP binding site/signaling complex. Annexin A2 (previously referred to as annexin II) is of particular interest because it has been shown to complex with CD44 in lipid rafts (19, 20), a unique cell surface microenvironment for receptor clustering and subsequent signaling. Annexin A2 is a widely expressed member of a family of $Ca^{2+}$-dependent phospholipid binding proteins and has been shown to participate in the formation of signaling complexes (21). To investigate the role of annexin A2 in mediating the cochemotactic activity of DBP, cells were pretreated with an affinity purified polyclonal anti-A2 or an irrelevant goat IgG and then allowed to migrate toward either C-activated serum or C-activated plasma. The result shows that anti-A2 significantly reduces U937-C5aR and neutrophil cell movement toward C-activated serum, but not C-activated plasma. Moreover, anti-A2 treatment did not alter chemotaxis to 1 nM purified C5a for either U937-C5aR cells (control, 48+/−5.5; anti-A2, 46+/−4.0 μm/120 min) or neutrophils (control, 48+/−3.6; anti-CD44, 48+/−4.4 μm/25 min). In addition, pretreatment of anti-A2 with its corresponding antigenic peptide (i.e., Ag blocking peptide) completely reversed the effect of anti-A2 on chemotaxis to C-activated serum. The experiment shows the analysis of annexin A2 and cell-associated DBP by confocal microscopy. The result showing the merged signal indicates considerable colocalization of the proteins on the cell surface. Finally, to determine whether anti-CD44 or anti-A2 blocks DBP binding to cells, U937-C5aR cells were pretreated with anti-CD44, anti-A2, both Abs, or an irrelevant goat IgG, and the binding of Alexafluor 488-labeled DBP was measured. The result demonstrates that either anti-CD44 or anti-A2 blocks DBP binding by almost 50%, whereas the combination of Abs reduces binding by ~75%, a significantly greater reduction (p<0.01) than either Ab alone. The added effect of dual Ab treatment on U937-C5aR cells was confirmed using the chemotaxis assay. A combination of anti-A2 and anti-CD44 showed an additional significant reduction (p<0.05) in cell movement to C-activated serum over anti-CD44 or anti-A2 alone, but had no effect on chemotaxis to C-activated plasma. These results indicate that both CD44 and annexin A2 are part of a cell surface DBP binding site complex and mediate the C5a chemotactic cofactor function of DBP.

| SEQUENCE LISTING |
| --- |
| 1. Full-length expressed DBP (residues #1-458) SEQ ID NO: 39 |
| LERGRDYEKN KVCKEFSHLG KEDFTSLSLV LYSRKFPSGT |
| FEQVSQLVKE VVSLTEACCA EGADPDCYDT RTSALSAKSC |
| ESNSPFPVHP GTAECCTKEG LERKLCMAAL KHQPQEFPTY |
| VEPTNDEICE AFRKDPKEYA NQFMWEYSTN YGQAPLSLLV |
| SYTKSYLSMV GSCCTSASPT VCFLKERLQL KHLSLLTTLS |
| NRVCSQYAAY GEKKSRLSNL IKLAQKVPTA DLEDVLPLAE |
| DITNILSKCC ESASEDCMAK ELPEHTVKLC DNLSTKNSKF |
| EDCCQEKTAM DVFVCTYFMP AAQLPELPDV ELPTNKDVCD |

```
                    -continued
                 SEQUENCE LISTING

PGNTKVMDKY TFELSRRTHL PEVFLSKVLE PTLKSLGECC

DVEDSTTCFN AKGPLLKKEL SSFIDKGQEL CADYSENTFT

EYKKKLAERL KAKLPDATPK ELAKLVNKRS DFASNCCSIN

SPPLYCDSEI DAELKNIL

2. Domains I & II (residues #1-378)
                    SEQ ID NO: 40

LERGRDYEKN KVCKEFSHLG KEDFTSLSLV LYSRKFPSGT

FEQVSQLVKE VVSLTEACCA EGADPDCYDT RTSALSAKSC

ESNSPFPVHP GTAECCTKEG LERKLCMAAL KHQPQEFPTY

VEPTNDEICE AFRKDPKEYA NQFMWEYSTN YGQAPLSLLV

SYTKSYLSMV GSCCTSASPT VCFLKERLQL KHLSLLTTLS

NRVCSQYAAY GEKKSRLSNL IKLAQKVPTA DLEDVLPLAE

DITNILSKCC ESASEDCMAK ELPEHTVKLC DNLSTKNSKF

EDCCQEKTAM DVFVCTYFMP AAQLPELPDV ELPTNKDVCD

PGNTKVMDKY TFELSRRTHL PEVFLSKVLE PTLKSLGECC

DVEDSTTCFN AKGPLLKK

3. Domain II & III (residues #192-458)
                    SEQ ID NO: 41

HLSLLTTLS NRVCSQYAAY GEKKSRLSNL IKLAQKVPTA

DLEDVLPLAE DITNILSKCC ESASEDCMAK ELPEHTVKLC

DNLSTKNSKF EDCCQEKTAM DVFVCTYFMP AAQLPELPDV

ELPTNKDVCD PGNTKVMDKY TFELSRRTHL PEVFLSKVLE

PTLKSLGECC DVEDSTTCFN AKGPLLKKEL SSFIDKGQEL

CADYSENTFT EYKKKLAERL KAKLPDATPK ELAKLVNKRS

DFASNCCSIN SPPLYCDSEI DAELKNIL

4. Domain II (residues #192-378) SEQ ID NO: 42

HLSLLTTLS NRVCSQYAAY GEKKSRLSNL IKLAQKVPTA

DLEDVLPLAE DITNILSKCC ESASEDCMAK ELPEHTVKLC

DNLSTKNSKF EDCCQEKTAM DVFVCTYFMP AAQLPELPDV

ELPTNKDVCD PGNTKVMDKY TFELSRRTHL PEVFLSKVLE

PTLKSLGECC DVEDSTTCFN AKGPLLKK

5. Domain III (residues #379-458) SEQ ID NO: 43

EL SSFIDKGQEL CADYSENTFT EYKKKLAERL

KAKLPDATPK ELAKLVNKRS DFASNCCSIN SPPLYCDSEI

DAELKNIL

6. Domain I (residues #1-191) SEQ ID NO: 44

LERGRDYEKN KVCKEFSHLG KEDFTSLSLV LYSRKFPSGT

FEQVSQLVKE VVSLTEACCA EGADPDCYDT RTSALSAKSC

ESNSPFPVHP GTAECCTKEG LERKLCMAAL KHQPQEFPTY

VEPTNDEICE AFRKDPKEYA NQFMWEYSTN YGQAPLSLLV

SYTKSYLSMV GSCCTSASPT VCFLKERLQL K

7. Domain I truncation (residues #1-175)
                    SEQ ID NO: 45

LERGRDYEKN KVCKEFSHLG KEDFTSLSLV LYSRKFPSGT

FEQVSQLVKE VVSLTEACCA EGADPDCYDT RTSALSAKSC

ESNSPFPVHP GTAECCTKEG LERKLCMAAL KHQPQEFPTY

VEPTNDEICE AFRKDPKEYA NQFMWEYSTN YGQAPLSLLV

SYTKSYLSMV GSCCT

8. Domain I truncation (residues #1-150)
                    SEQ ID NO: 46

LERGRDYEKN KVCKEFSHLG KEDFTSLSLV LYSRKFPSGT

FEQVSQLVKE VVSLTEACCA EGADPDCYDT RTSALSAKSC

ESNSPFPVHP GTAECCTKEG LERKLCMAAL KHQPQEFPTY

VEPTNDEICE AFRKDPKEYA NQFMWEYSTN

9. Domain I truncation (residues #1-125)
                    SEQ ID NO: 47

LERGRDYEKN KVCKEFSHLG KEDFTSLSLV LYSRKFPSGT

FEQVSQLVKE VVSLTEACCA EGADPDCYDT RTSALSAKSC

ESNSPFPVHP GTAECCTKEG LERKLCMAAL KHQPQEFPTY

VEPTN

10. Domain I truncation (residues #1-112)
                    SEQ ID NO: 48

LERGRDYEKN KVCKEFSHLG KEDFTSLSLV LYSRKFPSGT

FEQVSQLVKE VVSLTEACCA EGADPDCYDT RTSALSAKSC

ESNSPFPVHP GTAECCTKEG LERKLCMAAL KH
```

REFERENCES

1. White, P., and Cooke, N. *Trends Endocrinol. Metabol.* 11, 320-327 (2000).
2. Gomme, P. T., and Bertolini, J. *Trends Biotechnol.* 22, 340-345 (2004).
3. Hirschfeld, J. *Acta Pathol. Microbiol. Scand.* 47, 160 (1959).
4. Haddad, J. G., Hu, Y. Z., Kowalski, M. A., Laramore, C., Ray, K., Robzyk, P., and Cooke, N. E. *Biochemistry* 31, 7174-7181 (1992).
5. Swamy, N., Dutta, A., and Ray, R. *Biochemistry* 36, 7432-7436 (1997).
6. Verboven, C., Rabijns, A., De Maeyer, M., Van Baelen, H., Bouillon, R., and De Ranter, C. *Nat. Struct. Biol.* 9, 131-136 (2002).
7. Swamy, N., Head, J. F., Weitz, D., and Ray, R. *Arch. Biochem. Biophys.* 402, 14-23 (2002).
8. Head, J. F., Swamy, N., and Ray, R. *Biochemistry* 41, 9015-9020 (2002).
9. Otterbein, L. R., Cosio, C., Graceffa, P., and Dominguez, R. *Proc. Natl. Acad. Sci. USA* 99, 8003-8008 (2002).

10. Kohl, J. *Mol. Immunol.* 38, 175-187 (2001).
11. Gerard, N. P., and Gerard, C. *Nature.* 349, 614-617 (1991).
12. Kew, R. R., and Webster, R. O. *J. Clin. Invest.* 82, 364-369 (1988).
13. Perez, H. D., Kelly, E., Chenoweth, D., and Elfman, F. *J. Clin. Invest.* 82, 360-363 (1988).
14. Petrini, M., Azzara, A., Carulli, G., Ambrogi, F., and Galbraith, R. M. *J. Endocrinol. Invest.* 14, 405-408 (1991).
15. Metcalf, J. P., Thompson, A. B., Gossman, G. L., Nelson, K. J., Koyama, S., Rennard, S. I., and Robbins, R. A. *Am. Rev. Respir. Dis.* 143, 844-849 (1991).
16. Binder, R., Kress, A., Kan, G., Herrmann, K., and Kirschfink, M. *Mol. Immunol.* 36, 885-892 (1999).
17. Zwahlen, R. D., and Roth, D. R. *Inflammation* 14, 109-123 (1990).
18. Piquette, C. A., Robinson-Hill, R., and Webster, R. O. *J. Leukoc. Biol.* 55, 349-354 (1994).
19. Senior, R. M., Griffin, G. L., Perez, H. D., and Webster, R. O. *J. Immunol.* 141, 3570-3574 (1988).
20. Trujillo, G., and Kew, R. R. *J. Immunol.* 173, 4130-4136 (2004).
21. Swamy, N., Ghosh, S., and Ray, R. *Protein Express. Purif* 10, 115-122 (1997).
22. Merritt, J. E., McCarthy, S. A., Davies, M. P., and Moores, K. E. *Biochem. J.* 269, 513-519 (1990).
23. Kew, R. R., Mollison, K. W., and Webster, R. O. *J. Leukoc. Biol.* 58, 55-58 (1995).
24. Zigmond, S., and Hirsch, J. *J. Exp. Med.* 137, 387 (1973).
25. Kew, R. R., Fisher, J. A., and Webster, R. O. *J. Immunol.* 155, 5369-5374 (1995).
26. Cooke, N. E. *J. Biol. Chem.* 261, 3441-3450 (1986).
27. Yang, F., Bergeron, J. M., Linehan, L. A., Lalley, P. A., Sakaguchi, A. Y., and Bowman, B. H. *Genomics* 7, 509-516 (1990).
28. Osawa, M., Tsuji, T., Yukawa, N., Saito, T., and Takeichi, S. *Biochem. Mol. Biol. Int.* 34, 1003-1009 (1994).
29. He, X. M., and Carter, D. C. *Nature* 358, 209-215 (1992).
30. Mizwicki, M. T., and Norman, A. W. *J. Bone Miner. Res.* 18, 795-806 (2003).
31. DiMartino, S. J., and Kew, R. R. *J. Immunol.* 163, 2135-2142 (1999).
32. Nykjaer, A., Dragun, D., Walther, D., Vorum, H., Jacobsen, C., Herz, J., Melsen, F., Christensen, E. I., and Willnow, T. E. *Cell* 96, 507-515 (1999).
33. Nykjaer, A., Fyfe, J. C., Kozyraki, R., Leheste, J. R., Jacobsen, C., Nielsen, M. S., Verroust, P. J., Aminoff, M., de la Chapelle, A., Moestrup, S. K., Ray, R., Gliemann, J., Willnow, T. E., and Christensen, E. I. *Proc. Natl. Acad. Sci. USA* 98, 13895-13900 (2001).
34. Kanda, S., Mochizuki, Y., Miyata, Y., Kanetake, H., and Yamamoto, N. *J. Natl. Cancer Inst.* 94, 1311-1319 (2002).
35. Paul Licht and Leigh Hunt, Identification and Structural Characterization of a Novel Member of the Vitamin D Binding Protein family, <http://ist-socrates.berkeley.edu/~licht/DBPcDNA_abstract.htm>.

---

The invention claimed is:

1. An isolated Vitamin D Binding Protein (DBP) antagonist peptide consisting of EAFRKDPKEYANQFMWEYST (SEQ ID NO: 1).

2. A Vitamin D Binding Protein (DBP) antagonist peptide consisting of an amino acid sequence selected from the group consisting of:

| | | |
|---|---|---|
| (i) | EAFRKDPKEYANQFMWEYSTNYG; | (SEQ ID NO: 3) |
| (ii) | NYGQAPLSLLVSYTKSYLSMVGS; | (SEQ ID NO: 4) |
| (iii) | EAFRKDPKEYANQFMWEYS; | (SEQ ID NO: 5) |
| (iv) | EAFRKDPKEYANQFM; | (SEQ ID NO: 6) |
| (v) | DPKEYANQFMWEYST; | (SEQ ID NO: 7) |
| (vi) | EAFRKDPKEYAN; | (SEQ ID NO: 8) |
| (vii) | DPKEYANQFMWE; | (SEQ ID NO: 9) |
| (viii) | NQFMWEYSTNYG; | (SEQ ID NO: 10) |
| (ix) | YANQFMWEYST; | (SEQ ID NO: 11) |
| (x) | EAFRKDPKEY; | (SEQ ID NO: 12) |
| (xi) | ANQFMWEYST; | (SEQ ID NO: 13) |
| (xii) | DPKEYANQFM; | (SEQ ID NO: 14) |
| (xiii) | NQFMWEYST; | (SEQ ID NO: 15) |
| (xiv) | NQFMWEYS; | (SEQ ID NO: 16) |
| (xv) | QFMWEYST; | (SEQ ID NO: 17) |
| (xv) | NQFMWEY; | (SEQ ID NO: 18) |
| (xvi) | QFMWEYS; | (SEQ ID NO: 19) |
| (xvii) | FMWEYST; | (SEQ ID NO: 20) |
| (xviii) | EAFRKD; | (SEQ ID NO: 21) |
| (xix) | KEYANQ; | (SEQ ID NO: 22) |
| (xx) | YANQFM; | (SEQ ID NO: 23) |
| (xxi) | ANQFMW; | (SEQ ID NO: 24) |
| (xxii) | NQFMWE; | (SEQ ID NO: 25) |
| (xxiii) | QFMWEY; | (SEQ ID NO: 26) |
| (xxiv) | FMWEYS; | (SEQ ID NO: 27) |
| (xxv) | EAFRK; | (SEQ ID NO: 28) |
| (xxvi) | AFRKD; | (SEQ ID NO: 29) |
| (xxvii) | DPKEY; | (SEQ ID NO: 30) |
| (xxviii) | ANQFM; | (SEQ ID NO: 31) |
| (xxix) | WEYST; | (SEQ ID NO: 32) |
| (xxxi) | YANQF; | (SEQ ID NO: 33) |
| (xxxii) | ANQFM; | (SEQ ID NO: 34) |
| (xxxiii) | NQFMW; | (SEQ ID NO: 35) |
| (xxxiv) | QFMWE; | (SEQ ID NO: 36) |
| (xxxv) and | FMWEY; | (SEQ ID NO: 37) |
| (xxxvi) | MWEYS. | (SEQ ID NO: 38) |

3. A pharmaceutical composition comprising the isolated peptide of SEQ ID NO: 1 and a pharmaceutically acceptable carrier.

4. A pharmaceutical composition comprising the isolated peptide of claim 2 and a pharmaceutically acceptable carrier.

* * * * *